United States Patent [19]

Assmann et al.

[11] Patent Number: 5,922,881

[45] Date of Patent: Jul. 13, 1999

[54] HETEROCYCLIC IMINO DERIVATIVES

[75] Inventors: Lutz Assmann, Eutin; Thomas Seitz, Langenfeld; Ralf Tiemann, Leverkusen; Heinz-Wilhelm Dehne, Bonn; Klaus Stenzel, Düsseldorf, all of Germany

[73] Assignee: Bayer Aktiengesellschaft, Leverkusen, Germany

[21] Appl. No.: 08/737,952

[22] PCT Filed: May 22, 1995

[86] PCT No.: PCT/EP95/01933

§ 371 Date: Nov. 27, 1996

§ 102(e) Date: Nov. 27, 1996

[87] PCT Pub. No.: WO95/33717

PCT Pub. Date: Dec. 14, 1995

[30] Foreign Application Priority Data

Jun. 3, 1994 [GB] United Kingdom ............... 44 19 587

[51] Int. Cl.⁶ ............... C07D 207/22; C07D 263/16; C07D 277/18; A61K 31/40

[52] U.S. Cl. ............... 548/124; 548/194; 548/193; 548/195; 548/233; 548/236; 540/544; 540/596; 544/63; 504/219; 504/261; 504/266; 504/270; 504/223

[58] Field of Search ............... 548/124, 193, 548/194, 195, 233, 236; 504/219, 261, 266, 270, 223; 540/544, 596; 544/63

[56] References Cited

U.S. PATENT DOCUMENTS 5,663,185 9/1997 Mueller et al. ............... 514/365

FOREIGN PATENT DOCUMENTS

| 097614 | 6/1983 | European Pat. Off. . |
| 398692 | 5/1990 | European Pat. Off. . |
| 468775 | 7/1990 | European Pat. Off. . |
| 1920641 | 4/1969 | Germany . |
| 2709886 | 9/1977 | Germany . |
| 1595412 | 8/1981 | United Kingdom . |
| 9213830 | 8/1992 | WIPO . |

OTHER PUBLICATIONS

Farag et al. J. Pharm. Sci. 66, 423 (Mar. 1977).

*Primary Examiner*—José G. Dees
*Assistant Examiner*—Sabiha Qazi
*Attorney, Agent, or Firm*—Sprung Kramer Schaefer & Briscoe

[57] ABSTRACT

The invention relates to novel heterocyclic imino derivatives, several processes for their preparation and their use for controlling pests.

11 Claims, No Drawings

HETEROCYCLIC IMINO DERIVATIVES

This application has been filed under 35 USC 371 as a national Stage Application of PCT/EP95/01933, filed May 22, 1995.

The invention relates to novel heterocyclic imino derivatives, several processes for preparing them and their use for controlling pests.

It is known that various substituted alkoximino- and alkoxymethyleneacetamides have fungicidal properties (compare, for example, EP-A 398 692, EP-A 468 775, DE-A 40 30 038 and WO-A 92/13 830).

However, the efficacy of these previously disclosed compounds is not entirely satisfactory in all areas of application, especially at low application rates.

Novel heterocyclic imino derivatives of the general formula (I)

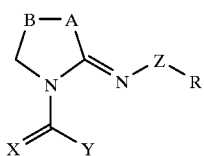
(I)

in which
A represents oxygen, sulphur or the $CH_2$ group,
B represents the $CH_2$ or the $CH_2CH_2$ group,
X represents the groups $=CHR^1$ or $=NR^2$, where
$R^1$ represents alkyl, alkoxy, althylthio, alkylamino and dialkylamino, which is in each case optionally substituted by halogen, cyano or alkoxy, and
$R^2$ represents amino or represents alkyl, alkoxy, alkylamino and dialkylamino, which is in each case optionally substituted by halogen, cyano or alkoxy,
Y represents the groups —CO-alkyl, —COOalkyl, —CO—NHalkyl, —CO—N(alkyl)$_2$, —CONR$^3$—OR$^4$ and

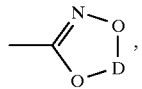

where
$R^3$ represents hydrogen or alkyl,
$R^4$ represents hydrogen or a group which can easily be eliminated, and
D represents optionally substituted alkanediyl,
Z represents a direct linkage; represents in each case optionally substituted alkylene, alkenylene and alkinylene, and represents the groups —(CHR$^5$)$_n$—O—, —(CHR$^5$)$_n$—S—, —(CHR$^5$)$_n$—NH—, —(CHR$^5$)$_n$—NR$^6$—, —(CHR$^5$)$_n$—SO—, —(CHR$^5$)$_n$—SO$_2$—, —(CHR$^5$)$_n$—O—SO—, —(CHR$^5$)$_n$—SO—O—, —(CHR$^5$)$_n$—O—SO$_2$, —(CHR$^5$)$_n$—SO$_2$—O—, —(CHR$^5$)$_n$—CO—, —(CHR$^5$)$_n$—CO—O—, —(CHR$^5$)$_n$—O—CO—, —(CHR$^5$)$_n$—CR$^6$=N—O—, —(CHR$^5$)$_n$—O—CO—, —(CHR$^5$)$_n$—CR$^6$=N—N=CR$^7$—, —(CHR$^5$)$_n$—N=CR$^7$—, —(CHR$^5$)$_n$—O—N=CR$^7$—, where
n represents the numbers 0, 1, 2, 3 or 4, where the radicals $R^5$ can be different when n is greater than 1; and
$R^5$, $R^6$ and $R^7$ independently of one another represent hydrogen, cyano and represent in each case optionally substituted alkyl, alkenyl, alkinyl or aryl; and
R represents hydrogen; halogen; represents in each case optionally substituted alkyl, alkenyl or alkinyl; and represents in each case optionally substituted cycloalkyl, cycloalkenyl, cycloalkinyl, heterocyclyl, aryl, heteroaryl, —(CHR$^5$)$_m$-cycloalkyl, —(CHR$^5$)$_m$-cycloalkenyl, —(CHR$^5$)$_m$-cycloalkinyl, —(CHR$^5$)$_m$-heterocyclyl, —(CHR$^5$)$_m$-aryl, —(CHR$^5$)$_m$-heteroaryl, —(CHR$^5$)$_m$—O-cycloalkyl, —(CHR$^5$)$_m$—O-cycloalkenyl, —(CHR$^5$)$_m$—O-cycloalkinyl, —(CHR$^5$)$_m$—O-heterocyclyl, —(CHR$^5$)$_m$—O-aryl, —(CHR$^5$)$_m$—O-heteroaryl, —(CHR$^5$)$_m$—S-cycloalkyl, —(CHR$^5$)$_m$—S-cycloalkenyl, —(CHR$^5$)$_m$—S-cycloalkinyl, —(CHR$^5$)$_m$—S-heterocyclyl, —(CHR$^5$)$_m$—S-aryl, —(CHR$^5$)$_m$—S-heteroaryl, —(CHR$^5$)$_m$—NH-cycloalkyl, —(CHR$^5$)$_m$—NH-cycloalkenyl, —(CHR$^5$)$_m$—NH-cycloalkinyl, —(CHR$^5$)$_m$—NH-heterocyclyl, —(CHR$^5$)$_m$—NH-aryl, —(CHR$^5$)$_m$—NH-heteroaryl, —(CHR$^5$)$_m$—NR$^6$-cycloalkyl, —(CHR$^5$)$_m$—NR$^6$-cycloalkenyl, —(CHR$^5$)$_m$—NR$^6$-cycloalkinyl, —(CHR$^5$)$_m$—NR$^6$-heterocyclyl, —(CHR$^5$)$_m$—NR$^6$-aryl, —(CHR$^5$)$_m$—NR$^6$-heteroaryl, where
$R^5$ and $R^6$ have the abovementioned meaning, and
m represents the numbers 1, 2, 3 or 4, where the radicals $R^5$ can be different when m is greater than 1, have been found.

It has furthermore been found that the novel heterocyclic imino derivatives of the formula (I) are obtained when
a) heterocyclic keto derivatives of the general formula (II)

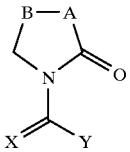
(II)

in which
A, B, X and Y have the abovementioned meaning,
are reacted with amines of the general formula (III)

H$_2$—N—Z—R (III)

in which
R and Z have the abovementioned meaning,
in the presence of a diluent and optionally in the presence of a reaction aid; or
b) heterocyclic keto derivatives of the general formula (II)

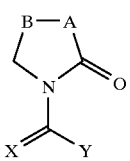
(II)

in which
A, B, X and Y have the abovementioned meaning,
are reacted with isocyanates of the general formula (IV)

OCN—Z—R (IV)

in which
R and Z have the abovementioned meaning,
optionally in the presence of a diluent; or
c) heterocyclic imino derivatives of the general formula (V)

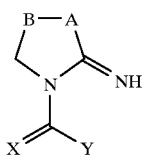 (V)

in which
A, B, X and Y have the abovementioned meaning,
are reacted with halogen derivatives of the general formula (VI)

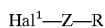 (VI)

in which
Hal$^1$ represents halogen, and
R and Z have the abovementioned meaning,
in the presence of a diluent and optionally in the presence of a reaction aid; or
d) heterocyclic imino derivatives of the general formula (VII)

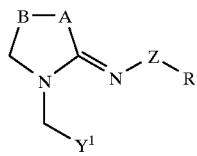 (VII)

in which
A, B, R and Z have the abovementioned meaning, and
Y$^1$ represents the groups —CO-alkyl or —COOalkyl,
are reacted initially with methyl formate and subsequently with an alkylating agent in the presence of a diluent and optionally in the presence of a reaction aid; or
e) heterocyclic imino derivatives of the general formula (VII)

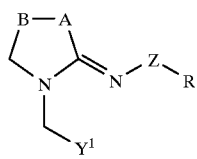 (VII)

in which
A, B, R and Z have the abovementioned meaning, and
Y$^1$ represents the groups —CO-alkyl or —COOalkyl,
are reacted with aldehydes of the general formula (IX)

 (IX)

in which
R$^1$ has the abovementioned meaning,
in the presence of a diluent and optionally in the presence of a reaction aid; or
f) heterocyclic imino derivatives of the general formula (VIII)

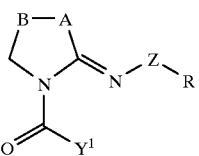 (VIII)

in which
A, B, R Y$^1$ and Z have the abovementioned meaning,
are reacted initially with hydroxylamine (optionally with its hydrohalide salts) and subsequently with an alkylating agent in the presence of a diluent and optionally in the presence of a reaction aid; or
g) heterocyclic imino derivatives of the general formula (X)

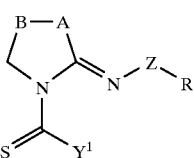 (X)

in which
A, B, R Y$^1$ and Z have the abovementioned meaning,
are reacted with amines of the general formula (XI)

 (XI)

in which
R$^2$ has the abovementioned meaning,
optionally with their hydrohalide salts in the presence of a diluent and optionally in the presence of a reaction aid; or
h) heterocyclic imino derivatives of the general formula (XII)

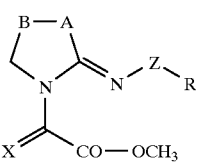 (XII)

in which
A, B, R, X and Z have the abovementioned meaning,
are reacted with amines of the general formula (XIII a) to (XIII c)

 (XIIIa)

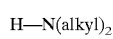 (XIIIb)

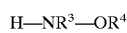 (XIIIc)

in which
R$^3$ and R$^4$ have the abovementioned meaning,
in the presence of a diluent and optionally in the presence of a reaction aid; or i) heterocyclic imino derivatives of the general formula (XII)

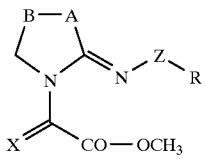

(XII)

in which

A, B, R, X and Z have the abovementioned meaning, are reacted in a first stage with hydroxylamine (or a hydrohalide thereof), optionally in the presence of an acid acceptor and optionally in the presence of a diluent, and in situ in a second stage with disubstituted alkanes of the general formula (XIV)

$$E-D-E \quad (XIV)$$

in which

D has the abovementioned meaning, and

E represents halogen, alkylsulphonyloxy or arylsulphonyloxy, optionally in the presence of a diluent and optionally in the presence of a reaction aid.

It has finally been found that the novel heterocyclic imino derivatives of the general formula (I) display potent fungicidal activity.

The compounds according to the invention may, where appropriate, be in the form of mixtures of various possible isomeric forms, in particular of E and Z isomers, but also, where appropriate, of optical isomers and diastereomers. Both the E and Z isomers, as well as any mixtures of the other possible isomers, are claimed.

The invention preferably relates to compounds of the formula (I) in which

A represents oxygen, sulphur or the $CH_2$ group.

B represents the $CH_2$ or the $CH_2CH_2$ group.

X represents the groups $=CHR^1$ or $=NR^2$, where $R^1$ represents alkyl, alkoxy, alkylthio, alkylamino and dialkylamino, which is in each case optionally substituted by halogen, cyano or $C_1$–$C_4$-alkoxy and has in each case 1 to 4 carbon atoms in the alkyl radicals, and $R^2$ represents amino or represents alkyl, alkoxy, alkylamino and dialkylamino, which is in each case optionally substituted by halogen, cyano or $C_1$–$C_4$-alkoxy and has in each case 1 to 4 carbon atoms in the alkyl radicals.

Y represents the groups —CO—$C_1$–$C_4$-alkyl, —CO—O—$C_1$–$C_4$-alkyl, —CO—NH—$C_1$–$C_4$-alkyl, —CO—N($C_1$–$C_4$-alkyl)$_2$, —CO—$NR^3$—$OR^4$ and

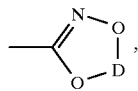

where $R^3$ represents hydrogen or $C_1$–$C_4$-alkyl, $R^4$ represents hydrogen, represents alkyl or alkenyl, which is in each case optionally substituted by halogen, $C_1$–$C_4$-alkoxy-$C_1$–$C_4$-alkoxy, N,N-di-($C_1$–$C_4$-alkyl)-amino, N-($C_1$–$C_4$-alkyl-carbonyl)-amino, N-($C_1$–$C_4$-alkyl)-N-($C_1$–$C_4$-alkyl-carbonylamino; N-($C_1$–$C_4$)-alkoxy-carbonyl)-amino or N-($C_1$–$C_4$-alkyl)-N-($C_1$–$C_4$)-alkoxy-carbonyl)-amino and has in each case 1 to 8 carbon atoms, represents $C_1$–$C_4$-alkoxy-carbonyl, represents $C_1$–$C_4$-alkylamino-carbonyl or represents di-($C_1$–$C_4$-alkyl)-aminocarbonyl; and D represents alkanediyl which is optionally substituted by halogen, $C_1$–$C_4$-alkyl or halogeno-$C_1$–$C_4$-alkyl and has 1 to 3 carbon atoms.

Z represents a direct linkage; represents $C_1$–$C_8$-alkylene, $C_2$–$C_8$-alkenylene and $C_2$–$C_8$-alkinylene, which is in each case optionally substituted by halogen, $C_1$–$C_4$-alkyl, halogeno-$C_1$–$C_4$-alkyl, nitro, cyano, $C_1$–$C_4$-alkoxy, halogeno-$C_1$–$C_4$-alkoxy, $C_1$–$C_4$-alkylthio and/or $C_1$–$C_4$-halogenoalkylthio; and represents the groups —$(CHR^5)_n$—O—, —$(CHR^5)_n$—S—, —$(CHR^5)_n$—NH—, —$(CHR^5)_n$—$NR^6$—, —$(CHR^5)_n$—SO—, —$(CHR^5)_n$—$SO_2$—, —$(CHR^5)_n$—O—SO—, —$(CHR^5)_n$—SO—O—, —$(CHR^5)_n$—O—$SO_2$, —$(CHR^5)_n$—$SO_2$—O—, —$(CHR^5)_n$—CO—, —$(CHR^5)_n$—CO—O—, —$(CHR^5)_n$—O—CO—, —$(CHR^5)_n$—$CR^6$=N—O—, —$(CHR^5)_n$—$CR^6$=N—N—$CR^7$—, —$(CHR^5)_n$—N=$CR^7$—, —$(CHR^5)_n$—O—N=$CR^7$—, where n represents the numbers 0, 1, 2, 3 or 4, where the radicals $R^5$ can be different when n is greater than 1; and $R^5$, $R^6$ and $R^7$ independently of one another represent hydrogen and represent $C_1$–$C_8$-alkyl, $C_2$–$C_8$-alkenyl, $C_2$–$C_8$-alkinyl or phenyl, which is in each case optionally substituted by halogen, $C_1$–$C_4$-alkyl, halogeno-$C_1$–$C_4$-alkyl, nitro, cyano, $C_1$–$C_4$-alkoxy, halogeno-$C_1$–$C_4$-alkoxy, $C_1$–$C_4$-alkylthio and/or $C_1$–$C_4$-halogenoalkylthio.

R represents hydrogen; halogen; represents $C_1$–$C_8$-alkyl, $C_2$–$C_8$-alkenyl or $C_2$–$C_8$-alkinyl, which is in each case optionally substituted by halogen, halogeno-$C_1$–$C_4$-alkyl, nitro, cyano, $C_1$–$C_4$-alkoxy, halogeno-$C_1$–$C_4$-alkoxy, $C_1$–$C_4$-alkylthio and/or $C_1$–$C_4$-halogenoalkylthio; and represents in each case optionally mono- to pentasubstituted, identically or differently, cycloalkyl with 3 to 7 carbon atoms, cycloalkenyl with 5 to 7 carbon atoms, aryl with 6 to 10 carbon atoms, (optionally benzo-fused) heterocyclyl (saturated or partially unsaturated) with 3 to 7 ring members, of which 1 to 3 represent hetero atoms such as N, O, and/or S atoms, and (optionally benzo-fused) heteroaryl with 5 or 6 ring members, of which one represents oxygen, sulphur or nitrogen and optionally one or two others represent nitrogen, where the substituents which are possible in each case are preferably selected from the following list:

oxygen (as replacement for two geminal hydrogen atoms), halogen, cyano, nitro, amino, hydroxyl, formyl, carboxyl, carbarnoyl, thiocarbamoyl, in each case straight-chain or branched alkyl, alkoxy, alkylthio, alkylsulphinyl or alkylsulphonyl with in each case 1 to 6 carbon atoms, in each case straight-chain or branched alkenyl or alkenyloxy with in each case 2 to 6 carbon atoms, in each case straight-chain or branched halogenoalkyl, halogenoalkoxy, halogenoalkylthio, halogenoalkylsulphinyl or halogenoalkylsulphonyl with in each case 1 to 6 carbon atoms and 1 to 13 identical or different halogen atoms, in each case straight-chain or branched halogenoalkenyl or halogenoalkenyloxy with in each case 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl with in each case 1 to 6 carbon atoms in the individual alkyl moieties, in each case optionally mono- or polysubstituted, identically or differently by halogen and/or straight-chain or branched alkyl with 1 to 4 carbon atoms and/or straight-chain or branched halogenoalkyl with 1 to 4 carbon atoms and 1 to 9 identical or different halogen atoms, and in each case doubly linked alkylene or dioxyalkylene with in each case 1 to 6 carbon atoms, cycloalkyl with 3 to 6 carbon atoms, heterocyclyl or heterocyclyl-methyl with in each case 3 to 7 ring members, of which in each case 1 to 3 are identical or different hetero atoms—in particular nitrogen, oxygen and/or sulphur—, and phenyl, pheoxy, benzyl, benzyloxy, phenylethyl or phenylethyloxy, which is in each case optionally mono- or polysubstituted in the phenyl moiety, identically or differently by halogen, cyano and/or straight-chain or branched alkyl with 1 to 4 carbon atoms and/or straight-chain or branched halogenoalkyl with 1 to 4 carbon atoms and 1 to 9 identical or different halogen atoms and/or straight-chain or branched alkoxy with 1 to 4 carbon atoms and/or straight-chain or branched halogenoalkoxy with 1 to 4 carbon atoms and 1 to 9 identical or different halogen atoms.

In the definitions, the saturated or unsaturated hydrocarbon chains, such as alkyl, alkanediyl, alkenyl or alkinyl, also when linked to heteroatoms, as in alkoxy, alkylthio or alkylamino, are in each case straight-chain or branched.

Halogen generally represents fluorine, chlorine, bromine or iodine, preferably represents fluorine, chlorine or bromine, in particular represents fluorine or chlorine.

The invention particularly relates to compounds of the formula (I) in which

A represents oxygen, sulphur or the $CH_2$ group.

B represents the $CH_2$ group or the $CH_2CH_2$ group.

X represents the groups $=CHR^1$ or $=NR^2$, where $R^1$ represents methyl, ethyl, propyl, methoxy, ethoxy, methylthio, ethylthio, methylamino, ethylamino or dimethylamino, which is in each case optionally substituted by fluorine, chlorine, cyano, methoxy or ethoxy, $R^2$ represents amino or represents methyl, ethyl, methoxy, ethoxy, methylamino, ethylamino or dimethylamino, which is in each case optionally substituted by fluorine, chlorine, cyano, methoxy or ethoxy.

Y represents the groups —$COCH_3$, —$COC_2H_5$, —$COC_3H_7$—n, —$COC_3H_7$—i, —$COOCH_3$, —$COOCH_2H_5$, —$COOC_3H_7$—n, —$COOC_3H_7$—i, —CO—$NHCH_3$, —CO—$NHC_2H_5$, —CO—$NHC_3H_7$—n, —CO—$NHC_3H_7$—i, —CO—$N(CH_3)_2$, —CO—$N(CH_3)C_2H_5$, —CO—$N(C_2H_5)_2$, —CO—$N(CH_3)C_3H_7$—n, —CO—$N(CH_3)C_3H_7$—i, —CO—$NR^3$—$OR^4$ and

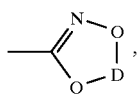

where $R^3$ represents hydrogen, methyl, ethyl, n- or i-propyl, and $R^4$ represents hydrogen, represents methyl, ethyl, n- or i-propyl, n-, i-, s- or t-butyl, which is optionally substituted by fluorine, chlorine, methoxy, ethoxy, n- or i-propoxy, methoxy-ethoxy, ethoxy-ethoxy, dimethylamino, diethylamino, acetylamino, propionylamino, N-methyl-acetylamino, N-ethyl-acetylamino, N-methyl-propionylamino, N-ethyl-propionylamino, methoxycarbonylamino, ethoxycarbonylamino, N-methyl-N-methoxycarbonylamino, N-ethyl-N-methoxycarbonylamino, N-methyl-N-ethoxycarbonylamino or N-ethyl-N-ethoxycarbonylamino, represents methoxycarbonyl, ethoxycarbonyl, methylaminocarbonyl, ethylaminocarbonyl, dimethylaminocarbonyl or diethylaminocarbonyl; and D represents methylene or ethane-1,2-diyl, which is in each case optionally substituted by fluorine, chlorine, methyl, ethyl or trifluoromethyl.

Z represents a direct linkage; represents —$CH_2$—, —$CH_2CH_2$—, —CH=CH—, —$CH_2O$—, —$CH_2S$—, —$CH_2NH$—, —$CH_2N(CH_3)$—, —N=CH—, —N=C($CH_3$)— and —N=C(CN)—, which is in each case optionally substituted by fluorine, chlorine, methyl, ethyl or trifluoromethyl.

R represents hydrogen; represents chlorine or bromine; represents methyl, ethyl and ethenyl, which is in each case optionally substituted by fluorine, chlorine or trifluoromethyl; represents cyclopropyl, cyclobutyl, cyclopentyl, cyclohexyl, cyclopentenyl or cyclohexenyl, which is in each case optionally mono- to trisubstituted, identically or differently, by fluorine, chlorine, bromine, cyano, carboxyl, phenyl, phenoxy (where phenyl and phenoxy are optionally substituted by fluorine, chlorine, bromine, cyano, methyl, ethyl, n- or i-propyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl; and represents phenyl, naphthyl, furyl, thienyl, oxazolyl, isoxazolyl, thiazolyl, isthiazolyl, oxadiazolyl, thiadiazolyl, pyridinyl, pyrimidinyl, pyridazinyl, pyrazinyl, 1,2,3-triazinyl, 1,2,4-triazinyl, 1,3,5-triazinyl, oxiranyl, tetrahydrofuryl, perhydropyranyl, pyrrolidinyl, piperidinyl or morpholinyl, which is in each case mono- to trisubstituted, identically or differently, where the possible substituents are preferably chosen from the following list: oxygen (as replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl; trimethylene (propane-1,3-diyl), methylenedioxy or ethylenedioxy, which is in each case optionally mono- or polysubstituted, identically or differently, by fluorine, chlorine, methyl, ethyl, n- or i-propyl, or cyclopropyl, cyclobutyl, cyclopentyl or cyclohexyl, and phenyl, phenoxy, benzyl or benzyloxy, which is in each case optionally mono- or polysubstituted, identically or differently, in the phenyl moiety by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

Very particularly preferred compounds are those of the general formulae (IA) to (ID):

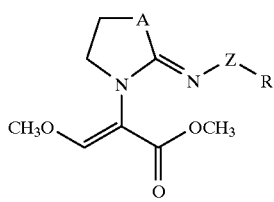
(IA)

in which

A, R and Z represent the abovementioned general, preferred and particularly preferred meanings.

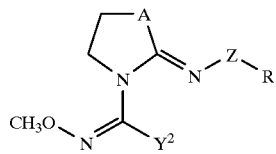
(IB)

in which

A, R and Z represent the abovementioned general, preferred and particularly preferred meanings, and $Y^2$ represents the groups —CO—OCH$_3$, —CO—NHCH$_3$, —CO—NHOH or

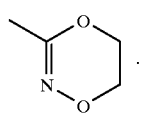

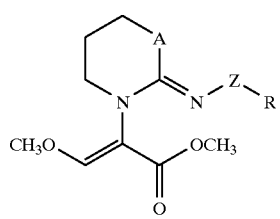
(IC)

in which

A, R and Z represent the abovementioned general, preferred and particularly preferred meanings.

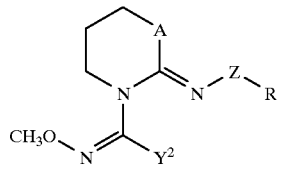
(ID)

in which

A, R and Z represent the abovementioned general, preferred and particularly preferred meanings, and $Y^2$ represents the groups —CO—OCH$_3$, —CO—NHCH$_3$, —CO—NHOH or

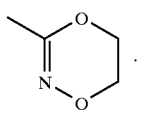

Also very particularly preferred are groups of substances of the general formulae (IA-1) to (IA-3) and (IB-1) to (IB-3):

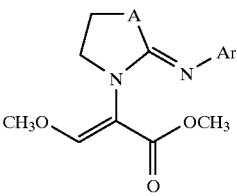
(IA-1)

in which

A represents the abovementioned meanings, and

Ar represents in each case optionally mono- to trisubstituted, identically or differently, phenyl or naphthyl, where suitable substituents are the phenyl substituents mentioned above under (R) as preferred and particularly preferred.

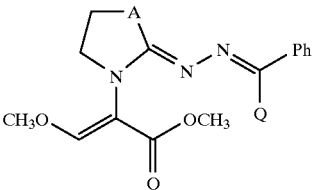
(IA-2)

in which

A represents the abovementioned meanings,

Q represents hydrogen, methyl or cyano, and

Ph represents optionally mono- to trisubstituted, identically or differently, phenyl, where suitable substituents are the phenyl substituents mentioned above under (R) as preferred and particularly preferred.

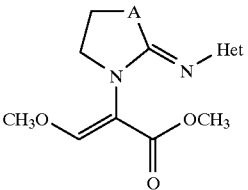
(IA-3)

in which

A represents the abovementioned meanings, and

Het represents in each case optionally mono- to trisubstituted, identically or differently, 5- or 6-membered heteroaryl such as, in particular, thiazolyl, thiadiazolyl, oxazolyl, oxadiazolyl, pyridinyl, pyrimidinyl or 1,3,5-triazinyl, where suitable substituents are the heteroaryl substituents mentioned above under (R) as preferred and particularly preferred.

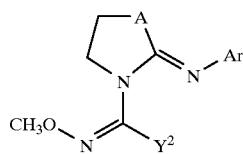
(IB-1)

in which

A represents the abovementioned meanings,

Y² represents the groups —CO—OCH₃, —CO—NHCH₃, —CO—NHOH or

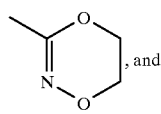, and

Ar represents in each case optionally mono- to trisubstituted, identically or differently, phenyl or naphthyl, where suitable substituents are the phenyl substituents mentioned above under (R) as preferred and particularly preferred.

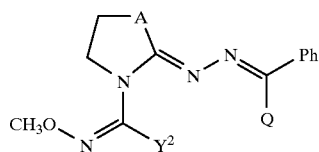
(IB-2)

in which

A represents the abovementioned meanings,

Q represents hydrogen, methyl or cyano,

Y² represents the groups —CO—OCH₃, —CO—NHCH₃, —CO—NHOH or

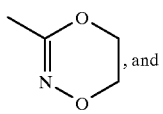, and

Ph represents optionally mono- to trisubstituted, identically or differently, phenyl, where suitable substituents are the phenyl substituents mentioned above under (R), as preferred and particularly preferred.

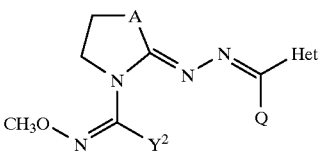
(IB-3)

in which

A represents the abovementioned meanings,

Y² represents the groups —CO—OCH₃, —CO—NHCH₃, —CO—NHOH or

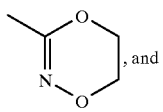, and

Het represents in each case optionally mono- to trisubstituted, identically or differently, 5- or 6-membered heteroaryl such as, in particular, thiazolyl, thiadiazolyl, oxazolyl, oxadiazolyl, pyridinyl, pyrimidinyl or 1,3,5-triazinyl, where suitable substituents are the heteroaryl substituents mentioned above under (R) as preferred and particularly preferred.

Examples of compounds according to the invention are listed in the following table:

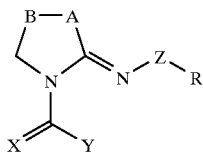
(I)

| A | B | X | Y | Z | R |
|---|---|---|---|---|---|
| CH₂ | CH₂ | CH₃OCH= | —COOCH₃ | — | ![phenoxy-chloro-cyanophenyl] |
| | | | | — | |
| O | CH₂ | CH₃OCH= | —COOCH₃ | — | ![dichlorophenyl] |
| | | | | — | |

-continued
$$\text{(I)}$$
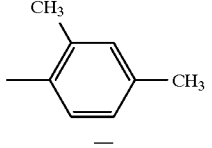
| A | B | X | Y | Z | R |
|---|---|---|---|---|---|
| O | CH$_2$ | CH$_3$OCH= | —COOCH$_3$ | — | 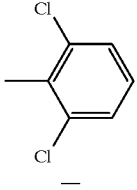 |
| O | CH$_2$ | CH$_3$ON= | —COOCH$_3$ | — | 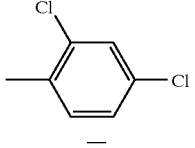 |
| O | CH$_2$ | CH$_3$ON= | —COOCH$_3$ | — | 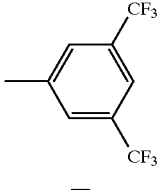 |
| O | CH$_2$ | CH$_3$ON= | —COOCH$_3$ | — | 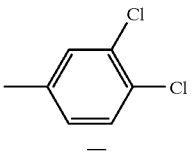 |
| O | CH$_2$ | CH$_3$ON= | —COOCH$_3$ | — | 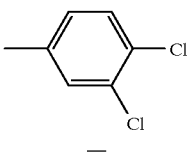 |
| CH$_2$ | CH$_2$ | CH$_3$OCH= | —COOCH$_3$ | — | 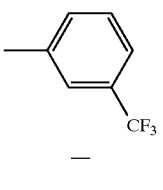 |
| CH$_2$ | CH$_2$ | CH$_3$OCH= | —COOCH$_3$ | — |  |

-continued
$$\begin{array}{c} \text{(I)} \\ \overset{B-A}{\underset{N}{\bigvee}}=N^{Z}\diagdown R \\ \underset{X}{\overset{\|}{C}}\diagdown Y \end{array}$$
| A | B | X | Y | Z | R |
|---|---|---|---|---|---|
| CH₂ | CH₂ | CH₃OCH= | —COOCH₃ | — | 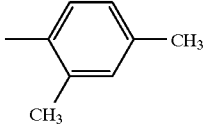 |
| CH₂ | CH₂ | CH₃OCH= | —COOCH₃ | — | 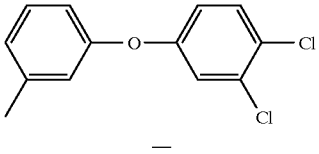 |
| CH₂ | CH₂ | CH₃OCH= | —COOCH₃ | — | 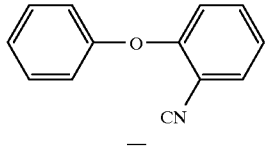 |
| CH₂ | CH₂ | CH₃OCH= | —COOCH₃ | — | 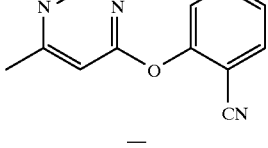 |
| CH₂ | CH₂ | CH₃OCH= | —COOCH₃ | — | 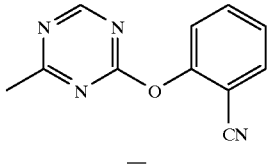 |
| CH₂ | CH₂ | CH₃ON= | —COOCH₃ | — | 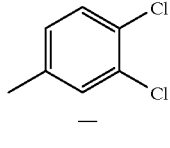 |
| CH₂ | CH₂ | CH₃ON= | —COOCH₃ | — | 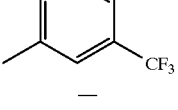 |
| CH₂ | CH₂ | CH₃ON= | —COOCH₃ | — | 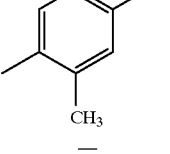 |

-continued
$$\text{(I)}$$
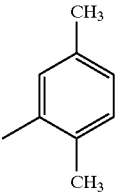
| A | B | X | Y | Z | R |
|---|---|---|---|---|---|
| CH$_2$ | CH$_2$ | CH$_3$ON= | —COOCH$_3$ | — | 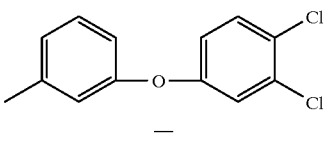 |
| CH$_2$ | CH$_2$ | CH$_3$ON= | —COOCH$_3$ | — | 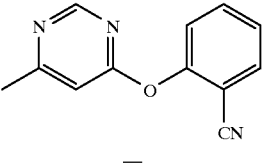 |
| CH$_2$ | CH$_2$ | CH$_3$ON= | —COOCH$_3$ | — | 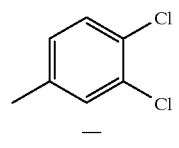 |
| CH$_2$ | CH$_2$ | CH$_3$ON= | —CONHCH$_3$ | — | 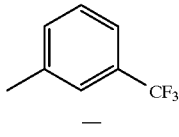 |
| CH$_2$ | CH$_2$ | CH$_3$ON= | —CONHCH$_3$ | — | 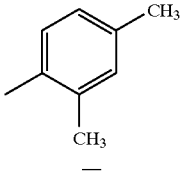 |
| CH$_2$ | CH$_2$ | CH$_3$ON= | —CONHCH$_3$ | — | 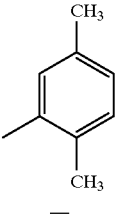 |
| CH$_2$ | CH$_2$ | CH$_3$ON= | —CONHCH$_3$ | — |  |

-continued $$\text{(I)}$$

Structure: 5-membered ring with B—A at top, CH₂—CH₂ at bottom, N in ring bonded to C(=N-Z-R) and to C(=X)(Y)

| A | B | X | Y | Z | R |
|---|---|---|---|---|---|
| CH₂ | CH₂ | CH₃ON= | —CONHCH₃ | — | 3-methylphenyl-O-(3,4-dichlorophenyl) |
| CH₂ | CH₂ | CH₃ON= | —CONHCH₃ | — | 6-methylpyrimidin-4-yl-O-(2-cyanophenyl) |
| CH₂ | CH₂ | CH₃ON= | 3-methyl-1,4,2-dioxazine | — | 3,4-dichlorophenyl |
| CH₂ | CH₂ | CH₃ON= | 3-methyl-1,4,2-dioxazine | — | 3-(trifluoromethyl)phenyl |
| CH₂ | CH₂ | CH₃ON= | 3-methyl-1,4,2-dioxazine | — | 2,4-dimethylphenyl (with CH₃ groups) |
| CH₂ | CH₂ | CH₃ON= | 3-methyl-1,4,2-dioxazine | — | 2,5-dimethylphenyl |
| CH₂ | CH₂ | CH₃ON= | 3-methyl-1,4,2-dioxazine | — | 3-methylphenyl-O-(3,4-dichlorophenyl) |
| CH₂ | CH₂ | CH₃ON= | 3-methyl-1,4,2-dioxazine | — | 6-methylpyrimidin-4-yl-O-(2-cyanophenyl) |

-continued
$$\text{(I)}$$
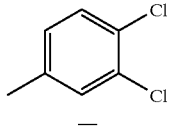
| A | B | X | Y | Z | R |
|---|---|---|---|---|---|
| O | CH$_2$ | CH$_3$OCH= | —COOCH$_3$ | — | 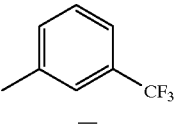 |
| O | CH$_2$ | CH$_3$OCH= | —COOCH$_3$ | — | 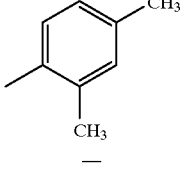 |
| O | CH$_2$ | CH$_3$OCH= | —COOCH$_3$ | — | 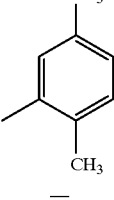 |
| O | CH$_2$ | CH$_3$OCH= | —COOCH$_3$ | — | 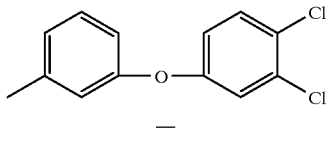 |
| O | CH$_2$ | CH$_3$OCH= | —COOCH$_3$ | — | 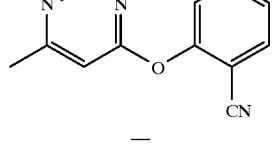 |
| O | CH$_2$ | CH$_3$OCH= | —COOCH$_3$ | — | 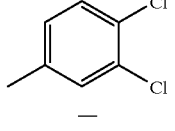 |
| O | CH$_2$ | CH$_3$ON= | —COOCH$_3$ | — | 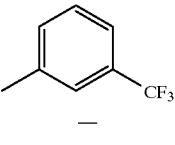 |
| O | CH$_2$ | CH$_3$ON= | —COOCH$_3$ | — |  |

-continued
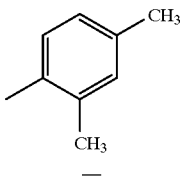
(I)
| A | B | X | Y | Z | R |
|---|---|---|---|---|---|
| O | CH₂ | CH₃ON= | —COOCH₃ | — | 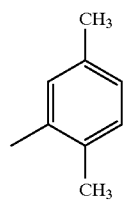 |
| O | CH₂ | CH₃ON= | —COOCH₃ | — | 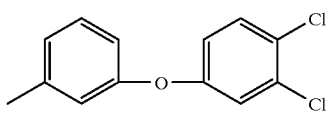 |
| O | CH₂ | CH₃ON= | —COOCH₃ | — | 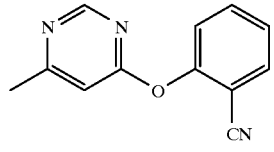 |
| O | CH₂ | CH₃ON= | —COOCH₃ | — | 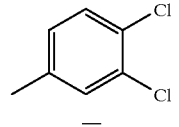 |
| O | CH₂ | CH₃ON= | —CONHCH₃ | — | 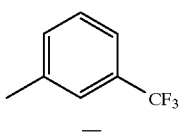 |
| O | CH₂ | CH₃ON= | —CONHCH₃ | — | 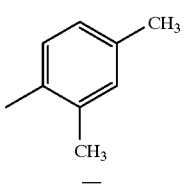 |
| O | CH₂ | CH₃ON= | —CONHCH₃ | — |  |

-continued
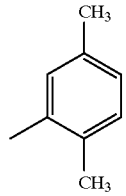
| A | B | X | Y | Z | R |
|---|---|---|---|---|---|
| O | CH$_2$ | CH$_3$ON= | —CONHCH$_3$ | — | 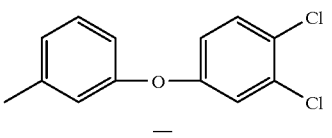 |
| O | CH$_2$ | CH$_3$ON= | —CONHCH$_3$ | — | 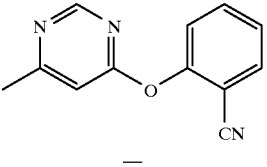 |
| O | CH$_2$ | CH$_3$ON= | —CONHCH$_3$ | — | 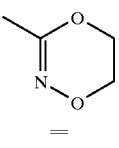 |
| O | CH$_2$ | CH$_3$ON= | 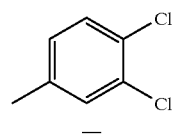 | — | 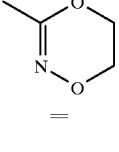 |
| O | CH$_2$ | CH$_3$ON= | 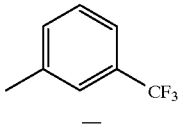 | — | 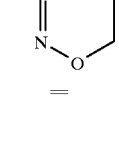 |
| O | CH$_2$ | CH$_3$ON= | 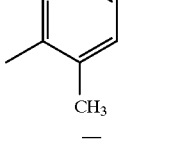 | — | 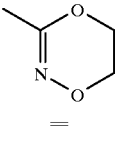 |
| O | CH$_2$ | CH$_3$ON= | 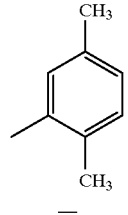 | — | (see above) |

-continued
$$\text{(I)}$$
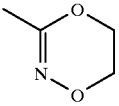
| A | B | X | Y | Z | R |
|---|---|---|---|---|---|
| O | CH$_2$ | CH$_3$ON= | 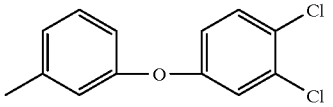 | — | 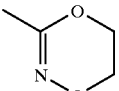 — |
| O | CH$_2$ | CH$_3$ON= | 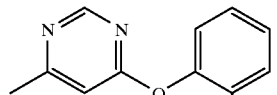 | — | 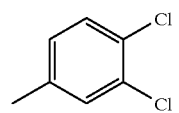 — |
| S | CH$_2$ | CH$_3$OCH= | —COOCH$_3$ | — | 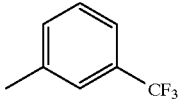 — |
| S | CH$_2$ | CH$_3$OCH= | —COOCH$_3$ | — | 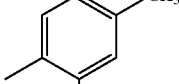 — |
| S | CH$_2$ | CH$_3$OCH= | —COOCH$_3$ | — | 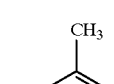 — |
| S | CH$_2$ | CH$_3$OCH= | —COOCH$_3$ | — | 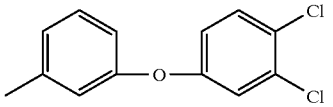 — |
| S | CH$_2$ | CH$_3$OCH= | —COOCH$_3$ | — | 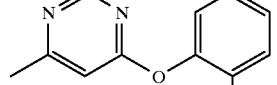 — |
| S | CH$_2$ | CH$_3$OCH= | —COOCH$_3$ | — | — |

-continued $$(I)$$

| A | B | X | Y | Z | R |
|---|---|---|---|---|---|
| S | CH₂ | CH₃OCH= | —COOCH₃ | —N=C(CH₃)— | 3-CF₃-phenyl |
| S | CH₂ | CH₃OCH= | —COOCH₃ | —N=C(CH₃)— | 3,4-dichlorophenyl |
| S | CH₂ | CH₃OCH= | —COOCH₃ | —N=CH— | 4-chlorophenyl |
| S | CH₂ | CH₃ON= | —COOCH₃ | — | 3,4-dichlorophenyl |
| S | CH₂ | CH₃ON= | —COOCH₃ | — | 3-CF₃-phenyl |
| S | CH₂ | CH₃ON= | —COOCH₃ | — | 2,5-dimethylphenyl |
| S | CH₂ | CH₃ON= | —COOCH₃ | — | 2,5-dimethylphenyl |
| S | CH₂ | CH₃ON= | —COOCH₃ | — | 3-(3,4-dichlorophenoxy)phenyl |

-continued
$$\text{(I)}$$
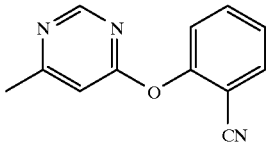
| A | B | X | Y | Z | R |
|---|---|---|---|---|---|
| S | CH₂ | CH₃ON= | —COOCH₃ | — | 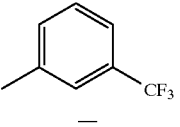 |
| S | CH₂ | CH₃ON= | —COOCH₃ | —N=C(CH₃)— | 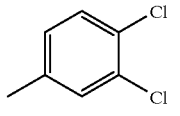 |
| S | CH₂ | CH₃ON= | —COOCH₃ | —N=C(CH₃)— | 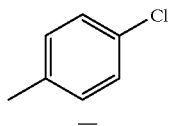 |
| S | CH₂ | CH₃ON= | —COOCH₃ | —N=CH— | 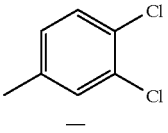 |
| S | CH₂ | CH₃ON= | —CONHCH₃ | — | 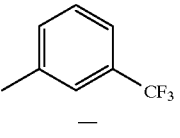 |
| S | CH₂ | CH₃ON= | —CONHCH₃ | — | 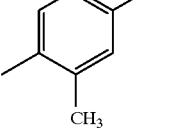 |
| S | CH₂ | CH₃ON= | —CONHCH₃ | — | 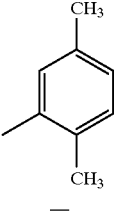 |
| S | CH₂ | CH₃ON= | —CONHCH₃ | — | |

-continued
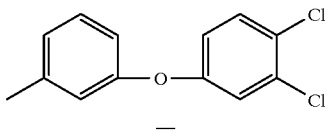
| A | B | X | Y | Z | R |
|---|---|---|---|---|---|
| S | CH$_2$ | CH$_3$ON= | —CONHCH$_3$ | — | 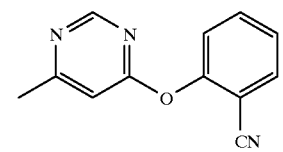 |
| S | CH$_2$ | CH$_3$ON= | —CONHCH$_3$ | — | 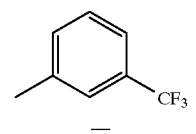 |
| S | CH$_2$ | CH$_3$ON= | —CONHCH$_3$ | —N=C(CH$_3$)— | 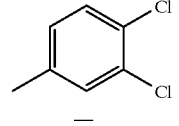 |
| S | CH$_2$ | CH$_3$ON= | —CONHCH$_3$ | —N=C(CH$_3$)— | 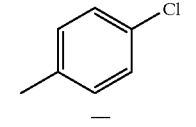 |
| S | CH$_2$ | CH$_3$ON= | —CONHCH$_3$ | —N=CH— | 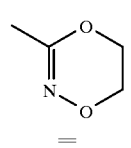 |
| S | CH$_2$ | CH$_3$ON= | 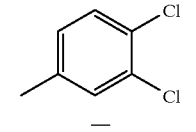 | — | 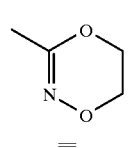 |
| S | CH$_2$ | CH$_3$ON= | 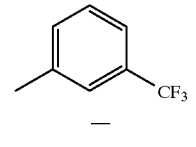 | — | 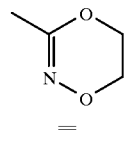 |
| S | CH$_2$ | CH$_3$ON= | 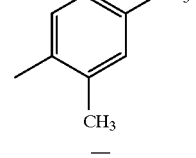 | — |  |

-continued

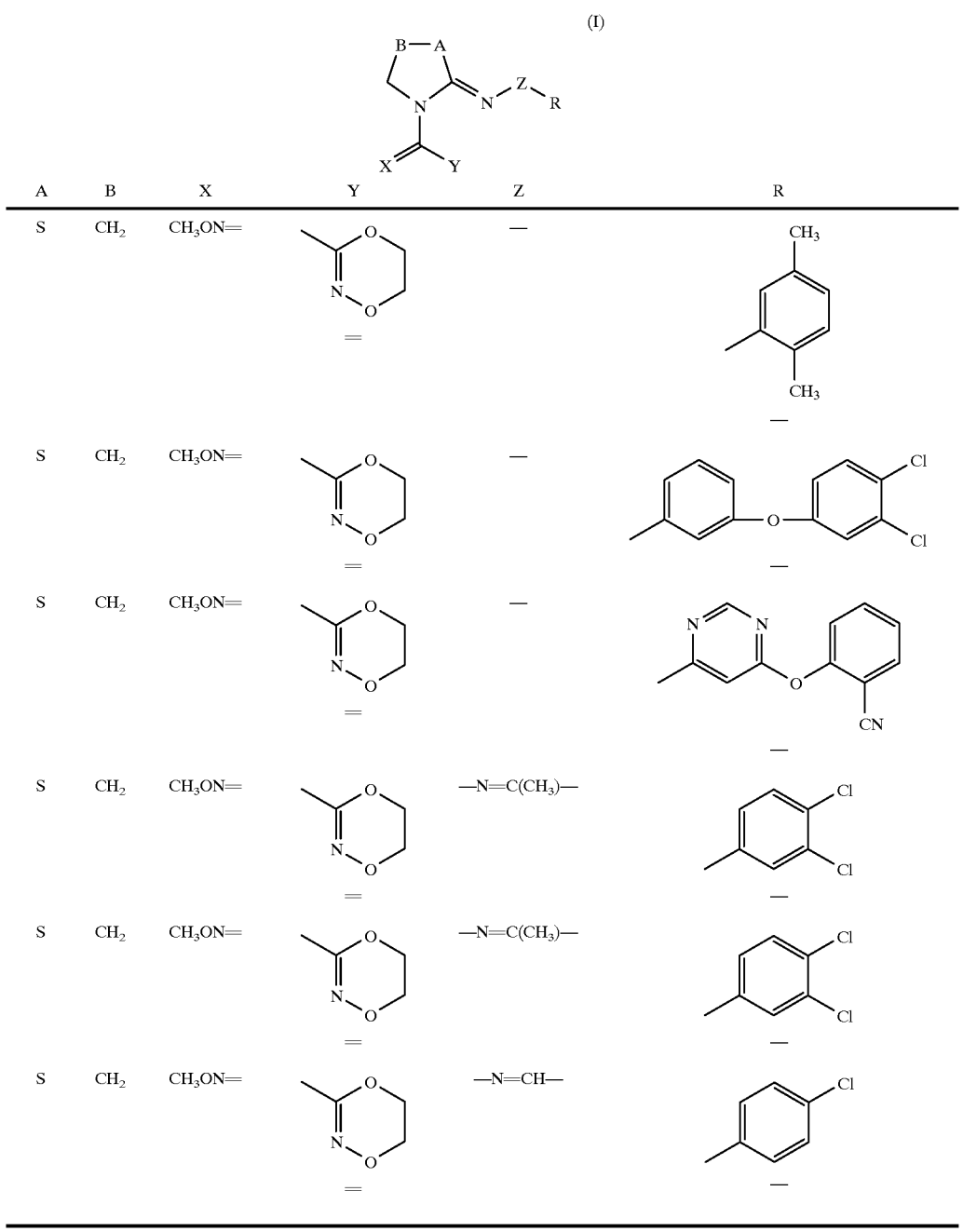

If, for example, N-(methoxycarbonyl-methoxyethylidene)-methyl-2-pyrrolidinone and aniline are used as starting materials, the course of the reaction in process (a) according to the invention can be outlined by the following formula diagram:

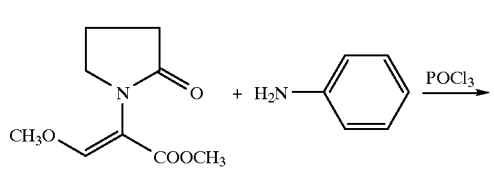

-continued

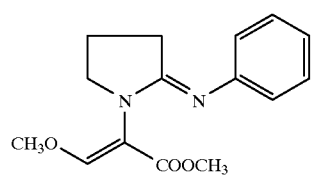

If, for example, N-(methoxycarbonyl-methoxyethylidene)-methyl-2-pyrrolidinone and chlorosulphone isocyanate are used as starting materials, the course of the reaction in process (b) according to the invention can be outlined by the following formula diagram:

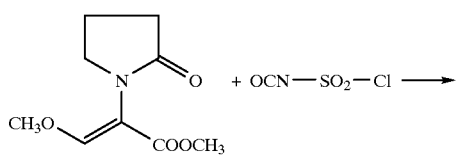

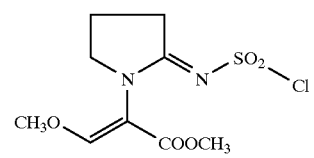

If, for example, N —(methoxycarbonyl-methoxyimino)-methyl-2-imino-oxazolidine and benzyl chloride are used as starting materials, the course of the reaction in process (c) according to the invention can be outlined by the following formula diagram:

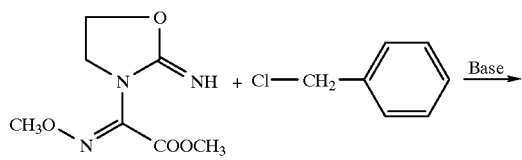

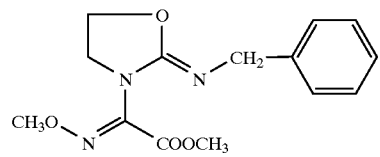

If, for example, N-methoxycarbonylmethyl-2-(2,6-dichlorophenyl)-imino-oxazolidine and methyl formate are used as starting materials, and dimethyl sulphate is used as alkylating agent, the course of the reaction in process (d) according to the invention can be outlined by the following formula diagram:

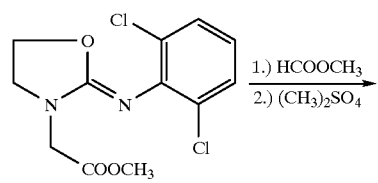

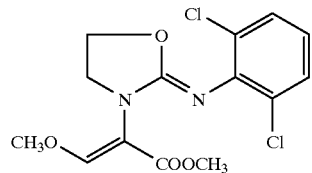

If, for example, N-methoxycarbonylmethyl-2-(2,6-dichlorophenyl)-imino-thiazolidine and n-butyraldehyde are used as starting materials, the course of the reaction in process (e) according to the invention can be outlined by the following formula diagram:

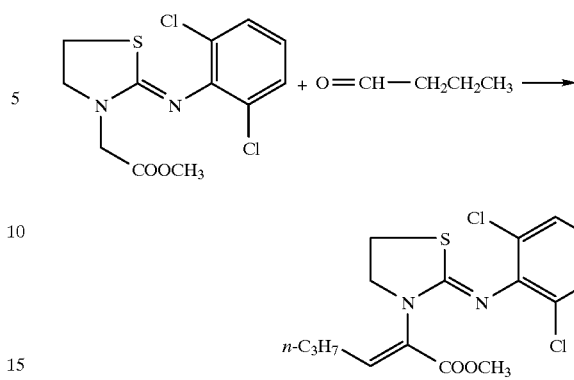

If, for example, methyl 2-(2-phenylimino-1pyrrolidinyl)-2-oxo-acetate and hydroxylamine are used as starting materials, methyl bromide is used as alkylating agent, the course of the reaction in process (f) according to the invention can be outlined by the following formula diagram:

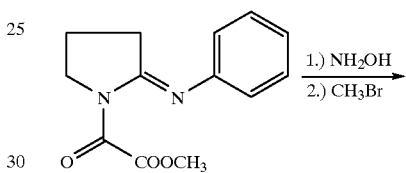

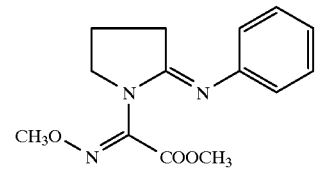

If, for example, methyl 2-(2-phenylimino-1-pyrrolidinyl)-2-thio-acetate and O-methylhydroxylammonium chloride are used as starting materials, the course of the reaction in process (g) according to the invention can be outlined by the following formula diagram:

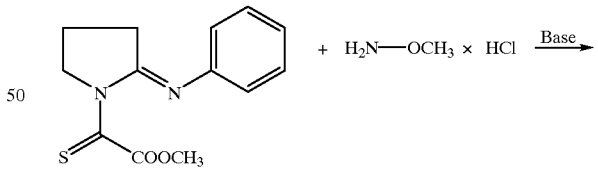

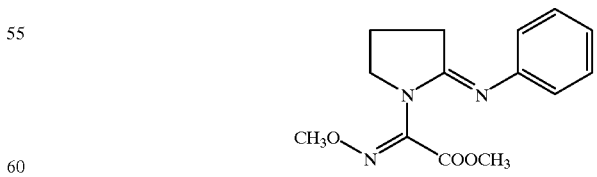

If, for example, N-(methoxycarbonyl-methoximino)-methyl-2-phenylimino-pyrrolidine and hydroxylamine hydrochloride are used as starting materials, the course of the reaction in process (h) according to the invention can be outlined by the following formula diagram:

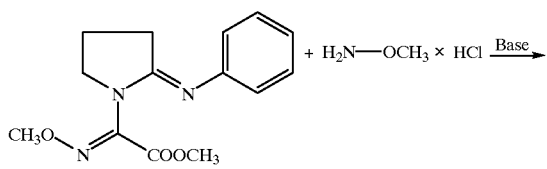

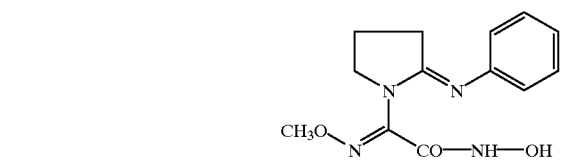

If, for example, N-(methoxycarbonyl-methoximino)-methyl-2-phenylimino-pyrrolidine, hydroxylamine hydrochloride and 1,2-dibromoethane are used as starting materials, the course of the reaction in process (i) according to the invention can be outlined by the following formula diagram:

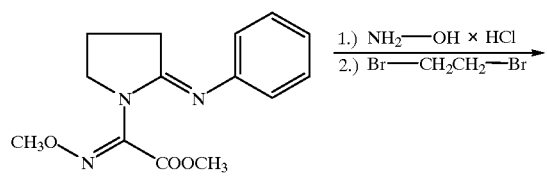

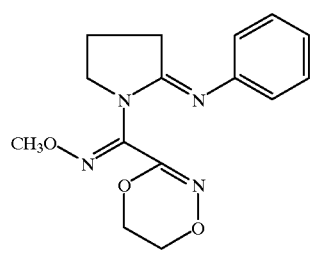

The heterocyclic keto derivatives required as starting materials for carrying out processes (a) and (b) according to the invention are generally defined by formula (II). In formula (II), A, B, X and Y have, preferably and in particular, those meanings which have already been mentioned above in connection with the description of the compounds of the formula (I) as preferred or as particularly preferred for these substituents.

The heterocyclic keto derivatives of the formula (II) have not yet been disclosed. However, they can be obtained by generally customary standard methods by reacting known heterocyclic ketones of the general formula (XV)

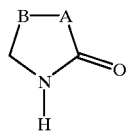 (XV)

in which
A and B have the abovementioned meaning,
with known halides of the general formula (XVI)

Hal²—CH₂—Y¹ (XVI)

in which
Hal² represents halogen, preferably chlorine or bromine, and
Y¹ has the abovementioned meaning,
where appropriate in the presence of a diluent such as, for example, tetrahydrofuran and, where appropriate, in the presence of a reaction aid such as, for example, sodium hydride, at temperatures between 0 and 100° C., further reacting the heterocyclic keto derivatives, obtained in this way, of the general formula (XVII)

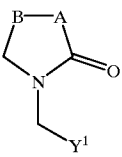 (XVII)

in which
A, B and Y¹ have the abovementioned meaning, by processes (d), (e), (h) and/or (i) (also compare in this connection the preparation examples).

The amines and isocyanates which are additionally required as starting materials for carrying out processes (a) and (b) according to the invention are generally defined by formulae (III) and (IV) respectively. In formulae (III) and (IV), Z and R have, preferably and in particular, those meanings which have already been mentioned above in connection with the description of the compounds of the formula (I) as preferred and as particularly preferred for these substituents.

The amines of the formula (III) and the isocyanates of the formula (IV) are generally known compounds of organic chemistry and are obtainable by standard methods described in the literature.

The heterocyclic imino derivatives required as starting materials for carrying out process (c) according to the invention are generally defined by formula (V). In formula (V) A, B, X and Y have, preferably and in particular, those meanings which have already been mentioned above in connection with the description of the compounds of the formula (I) as preferred and as particularly preferred for these substituents.

The heterocyclic imino derivatives of the formula (V) have not yet been disclosed. However, they can be obtained in a generally known manner by heating heterocyclic keto derivatives of the general formula (II) with chlorosulphonyl isocyanate in the presence of a diluent such as, for example, chloroform under reflux (also compare in this connection the preparation examples).

The halogen derivatives additionally required as starting materials for carrying out process (c) according to the invention are generally defined by formula (VI). In formula (VI), R and Z have, preferably and in particular, those meanings which have already been mentioned above in connection with the meaning of the compounds of the formula (I) as preferred and as particularly preferred for the substituents. Hal¹ preferably represents chlorine or bromine.

The halogen derivatives of the formula (VI) are generally known compounds of organic chemistry.

The heterocyclic imino derivatives required as starting materials for carrying out processes (b) and (e) according to the invention are generally defined by formula (VII). In formula (VII), A, B, R and Z have, preferably and in particular, those meanings which have already been mentioned above in connection with the description of the compounds of the formula (I) as preferred and as particularly preferred for these substituents.

$Y^1$ preferably and in particular represents those meanings of the groups —CO-alkyl and —COOalkyl which have already been mentioned above in connection with the description of the compounds of the formula (I) as preferred and as particularly preferred for these groups.

The heterocyclic imino derivatives of the formula (VII) have not yet been disclosed. However, they can be obtained by generally customary standard methods by reacting imino derivatives of the general formula (XVIII)

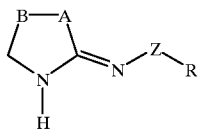
(XVIII)

in which

A, B, R and Z have the abovementioned meanings, with known halides of the formula (XVI), where appropriate in the presence of a diluent such as, for example, tetrahydrofuran and, where appropriate, in the presence of a reaction aid such as potassium tert-butoxide, at temperatures between 0 and 100° C. (also compare in this connection the preparation examples).

The imino derivatives of the formula (VIII) are known (compare, for example, DE-OS (German Published Specification) 19 63 192, DE-OS (German Published Specification) 30 47 759, JP 76-12 44 75, Tetrahedron Letters 22(45), 4471–4), and can be obtained by the processes described therein or others which are generally known.

Alkylating agents suitable for carrying out processes (d) and (f) according to the invention are customary reagents such as, for example, alkyl halides, in particular methyl chloride, methyl bromide and methyl iodide, and dialkyl sulphates such as, in particular, dimethyl sulphate.

The alkylating agents are generally known compounds of organic chemistry.

The aldehydes additionally required as starting materials for carrying out process (e) according to the invention are generally defined by formula (IX). In formula (IX), $R^1$ has, preferably and in particular, those meanings which have already been mentioned above in connection with the description of the compounds of the formula (I) as preferred and as particularly preferred for these substituents.

The aldehydes of the formula (IX) are generally known compounds of organic chemistry.

The heterocyclic imino derivatives required as starting materials for carrying out process (f) according to the invention are generally defined by formula (VIII). In formula (VIII), A, B, R and Z have, preferably and in particular, those meanings which have already been mentioned above in connection with the description of the compounds of the formula (I) as preferred and as particularly preferred for these substituents.

The heterocyclic imino derivatives of the formula (VIII) have not yet been disclosed. However, they can be obtained by generally customary standard methods by reacting imino derivatives of the general formula (XVIII) with known keto halides of the general formula (XIX)

 (XIX)

in which $Hal^3$ represents halogen, preferably chlorine or bromine, and $Y^1$ has the abovementioned meaning, where appropriate in the presence of a diluent, such as, for example, tetrahydrofuran and, where appropriate, in the presence of a reaction aid such as, for example, potassium carbonate, at temperatures between 0 and 100° C. (also compare in this connection the preparation examples).

The heterocyclic imino derivatives required as starting materials for carrying out process (g) according to the invention are generally defined by formula (X). In formula (X), A, B and Z have, preferably and in particular, those meanings which have already been mentioned above in connection with the description of the compounds of the formula (I) as preferred and as particularly preferred for these substituents.

$Y^1$ preferably and in particular represents those meanings of the groups —CO-alkyl and —COO alkyl which have already been mentioned above in connection with the description of the compounds of the formula (I) as preferred and as particularly preferred for these groups.

The heterocyclic imino derivatives of the formula (X) have not yet been disclosed. However, they can be obtained by standard methods described in the literature, by, for example, reacting the corresponding keto derivatives of the general formula (VIII) with a sulphurizing agent such as, for example, $P_4S_{10}$ or Lawesson's reagents [2,4-bis(4-methoxyphenyl)-1,3,2,4-dithiadiphosphetane-2,4-dithione], where appropriate in a diluent such as, for example, xylene or toluene, at temperatures between 80 and 200° C.

The amines which are additionally required as starting materials for carrying out process (d) according to the invention are generally defined by formula (XI). In formula (XI), $R^1$ has, preferably and in particular, those meanings which have already been mentioned above in connection with the description of the compounds of the formula (I) as preferred and as particularly preferred for this substituent.

The amines of the formula (XI) are generally known compounds of organic chemistry.

The heterocyclic imino derivatives required as starting materials for carrying out processes (h) and (i) according to the invention are generally defined by formula (XII). In formula (XII), A, B, R, X and Y have, preferably and in particular, those meanings which have already been mentioned above in connection with the description of the compounds of the formula (I) as preferred and as particularly preferred for these substituents.

The heterocyclic imino derivatives of the formula (XII) are compounds according to the invention.

The amines additionally required as starting materials for carrying out process (h) according to the invention are generally defined by formulae (XIIIa), (XIIIb) and (XIIIc).

In formulae (XIIIa) and (XIIIb), alkyl has, preferably and in particular, those meanings which have already been mentioned above in connection with the description of the compounds of the formula (I) as preferred and as particularly preferred for alkyl in the substituents Y=—CO—NH alkyl and —CO—N(alkyl)$_2$.

In formula (XIIIc), $R^3$ and $R^4$ have, preferably and in particular, those meanings which have already been mentioned above in connection with the description of the compounds of the formula (I) as preferred and as particularly preferred for these substituents.

The amines of the formulae (XIIIa), (XIIIb) and (XIIIc) are generally known compounds of organic chemistry.

The disubstituted alkanes additionally required as starting materials for carrying out process (i) according to the invention are generally described by formula (XIV). In formula (XIV), D has, preferably and in particular, those meanings which have already been mentioned above in connection with the description of the compounds of the formula (I) as preferred and as particularly preferred for this substituent.

E preferably represents chlorine, bromine, iodine, methanesulphonyloxy or p-toluenesulphinyloxy.

The disubstituted alkanes of the formula (XIV) are generally known compounds of organic chemistry.

Suitable diluents for carrying out processes (a) to (i) according to the invention are inert organic solvents. Those which can preferably be used are aliphatic, alicyclic or aromatic, optionally halogenated hydrocarbons such as, for example, benzine, benzene, toluene, xylene, chlorobenzene, petroleum ether, hexane, cyclohexane, dichloromethane, chloroform, tetrachloromethane, ethers such as diethyl ether, dioxane, tetrahydrofuran or ethylene glycol dimethyl or diethyl ether, nitriles such as acetonitrile or propionitrile, amides such as dimethylformamide, dimethylacetamide, N-methylformanilide, N-methylpyrrolidone or hexamethylphosphoric amide, esters such as ethyl acetate or sulphoxides such as dimethyl sulphoxide, alcohols such as methanol or ethanol or basic solvents such as pyridine or triethylamine.

Process (a) according to the invention is preferably carried out in the presence of a dehydrating agent as reaction aid. Phosphorus oxychloride can preferably be used (compare, for example, J. Med. Chem. 18 (1975) 90–99).

Processes (c) and (i) according to the invention are preferably carried out in the presence of a suitable reaction aid. Suitable as such are all inorganic and organic bases which can normally be used. Alkali metal hydrides, hydroxides, alcoholates, carbonates or bicarbonates are preferably used, such as, for example, sodium hydroxide, sodium methoxide, sodium ethoxide, potassium t-butoxide, sodium carbonate, potassium carbonate or sodium bicarbonate or else tertiary amines such as, for example, triethylamine, N,N-deimethylaniline, pyridine, N,N-dimethylaminopyridine, diazabicyclooctane (DABCO), diazabicyclononene (DBN) or diazabicycloundecene (DBU). Acidic reaction aids such as, for example, p-toluenesulphonic acid are also advantageous where appropriate.

The reaction temperatures when carrying out processes (a) to (i) according to the invention can be varied within a relatively wide range. The temperatures employed are generally between 0° C. and +200° C., preferably temperatures between 20° C. and 150° C.

Process (a) according to the invention is carried out using, per mole of heterocyclic keto derivative of the formula (II), in general 1 to 4 mol, preferably 1 to 2 mol, of amine and 1 to 6 mol, preferably 1 to 4 mol, of dehydrating agent as reaction aid.

Process (b) according to the invention is carried out using, per mole of heterocyclic keto derivative of the formula (II), in general 1 to 3 mol, preferably 1 to 2 mol, of isocyanate of the formula (IV).

Process (c) according to the invention is carried out using, per mole of heterocyclic imino derivative of the formula (V), in general 1 to 3 mol, preferably 1 to 2 mol, of halogen derivative of the formula (VI) and, where appropriate, 1 to 6 mol, preferably 1 to 4 mol, of reaction aid.

Process (d) according to the invention is carried out using, per mole of heterocyclic imino derivative of the formula (VII), in general 1 to 30 mol, preferably 1 to 25 mol, of methyl formate (where appropriate simultaneously as solvent) and 1 to 4 mol, preferably 1 to 2 mol, of alkylating agent and, where appropriate, 1 to 8 mol, preferably 1 to 4 mol, of reaction aid.

Process (e) according to the invention is carried out using, per mole of heterocyclic imino derivative of the formula (VII), in general 1 to 3 mol, preferably 1 to 2 mol, of aldehyde of the formula (IX) and, where appropriate, 1 to 6 mol, preferably 1 to 4 mol, of reaction aid.

Process (f) according to the invention is carried out using, per mole of heterocyclic imino derivative of the formula (VIII), in general 1 to 3 mol, preferably 1 to 2 mol, of hydroxylamine or of an appropriate hydrohalide and 1 to 3 mol, preferably 1 to 2 mol, of alkylating agent and, where appropriate, 1 to 6 mol, preferably 1 to 4 mol, of reaction aid.

The appropriate alkylated hydroxylamine derivative can also, where appropriate, be employed directly.

Process (g) according to the invention is carried out using, per mole of heterocyclic imino derivative of the formula (X), in general 1 to 4 mol, preferably 1 to 2 mol, of amine or of the appropriate hydrohalide and, where appropriate, 1 to 3 mol, preferably 1 to 2 mol, of reaction aid.

Process (h) according to the invention is carried out using, per mole of heterocyclic imino derivative of the formula (VII), in general 1 to 3 mol, preferably 1 to 1.5 mol, of amine of the formulae (XIIIa), (XIIIb) and (XIIIc) and, where appropriate, 0.1 to 3 mol, preferably 0.5 to 1.5 mol, of reaction aid.

Process (i) according to the invention is carried out using, per mole of heterocyclic imino derivative of the formula (XII), in general 1 to 5 mol, preferably 1 to 2.5 mol, of hydroxylamine or of the appropriate hydrohalide and, in general, 1 to 10 mol, preferably 1 to 5 mol, of disubstituted alkane of the formula (XIV) and, where appropriate, 1 to 5 mol, preferably 1 to 2.5, mol of reaction aid.

The reaction is carried out and worked up, and the reaction products are isolated by generally customary and known methods in all the processes.

The active substances according to the invention have a potent microbicidal effect and can be employed in practice for controlling unwanted microorganisms. The active substances are suitable for use as crop protection agents, in particular as fungicides.

Fungicidal compositions are employed in crop protection to control Plasmodiophoromycetes, Oomycetes, Chytridiomycetes, Zygomycetes, Ascomycetes, Basidiomycetes, Deuteromycetes.

Some causes of fungal diseases which are covered by the general terms listed above may be mentioned by way of example but without limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturai species, such as, for example, *Venturia inaequalis;*

Pyrenophora species, such as, for example, *Pyrenophora teres* or *Pyrenophora graminea* (conidiaform: Drechslera, synonym: Helminthosporium);

Cochliobolus species, such as, for example, *Cochliobolus sativus* (conidaform: Drechslera, synonym: Helminthosporium);

Uromyces species, such as, for example, *Uromyces appendiculatus;*

Puccinia species, such as, for example, *Pucinnia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

Very good tolerability of the active substances by plants at the concentrations necessary to control plant diseases allow treatment of the above-ground parts of plants, of plant and seed materials and of the soil.

In this connection, the active substances according to the invention can be used particularly successfully for controlling diseases in fruit and vegetable crops such as, for example, against Podosphaera species, or for controlling diseases of rice, such as, for example, against *Pyricularia oryzae.*

The active substances can be converted into customary formulations depending on their respective physical and/or chemical properties, such as solutions, emulsions, suspensions, powders, foams, pastes, granules, aerosols, microencapsulations in polymeric materials and in coating compositions for seeds, and ULV cooled and warm fogging formulations.

These formulations are produced in a known manner, for example by mixing the active substances with extenders, that is to say liquid solvents, liquefied gases which are under pressure and/or solid carriers, where appropriate using surface-active agents, that is to say emulsifiers and/or dispersants and/or foam-generating agents. In the event that water is used as extender it is possible, for example, also to use organic solvents as auxiliary solvents. Suitable liquid solvents are essentially: aromatic compounds such as xylene, toluene, alkylnaphthalenes, chlorinated aromatic compounds or chlorinated aliphatic hydrocarbons, such as chlorobenzenes, chloroethylenes, or methylene chloride, aliphatic hydrocarbons such as cyclohexane or paraffins, for example petroleum fractions, alcohols such as butanol or glycol, and their ethers and esters, ketones such as acetone, methyl ethyl ketone, methyl isobutyl ketone or cyclohexanone, highly polar solvents such as dimethyl formamide or dimethyl sulphoxide, and water; liquefied gaseous extenders or carriers meaning liquids which are gaseous at normal temperature and under atmospheric pressure, for example aerosol propellant gases such as halogenated hydrocarbons, and butane, propane, nitrogen and carbon dioxide; suitable solid carriers are: for example natural rock powders such as kaolins, aluminas, talc, chalk, quartz, attapulgite, montmorillonite or diatomaceous earth and synthetic rock powders such as highly disperse silica, aluminium oxide and silicates; suitable solid carriers for granules are: for example crushed and fractionated natural rocks such as calcite, marble, pumice, sepiolite, dolomite and synthetic granules of inorganic and organic powders, and granules from organic materials such as sawdust, coconut shells, corn stalks and tobacco stalks; suitable emulsifiers and/or foam-generating agents are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin sulphite waste liquors and methylcellulose.

It is possible to use in the formulations adhesives such as carboxymethylcellulose, natural and synthetic, powdered, granular or latex-like polymers such as gum arabic, polyvinyl alcohol, polyvinyl acetate, and natural phospholipids such as cephalins and lecithins and synthetic phospholipids. Other possible additives are mineral and vegetable oils.

It is possible to use colouring agents such as inorganic pigments, for example iron oxide, titanium oxide, Prussian blue and organic colouring agents such as alizarin, azo and metal phthalocyanine dyes and trace nutrients such as salts of iron, manganese, boron, copper, cobalt, molybdenum and zinc.

The formulations generally contain between 0.1 and 95% by weight of active substance, preferably between 0.5 and 90%.

The active substances according to the invention can be used as such or in their formulations also mixed with known fimgicides, bactericides, acaricides, nematicides or insecticides in order thus, for example, to widen the spectrum of action or prevent development of resistance.

Suitable for mixtures are, for example:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thizole-5-carboxanilide; 2,6-dichloro-N-(4-trifluoromethylbenzyl)benzamide; (E)-2-methoxyimino-N-methyl-2-(2-phenoxyphenyl) acetamide; 8-hydroxyquinoline sulphate; methyl (E)-2-{2-[6-(2-cyanophenoxy)pyrimidin-4-yloxy]phenyl}-3-methoxyacrylate; methyl (E)-methoxyimino [alpha-(o-tolyloxy)-o-tolyl] acetate; 2-phenylphenol (OPP), aldimorph, ampropylfos, anilazin, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, chinomethionate (quinomethionate), chloroneb, chloropicrin, chlorothalonil, chlozolinate, cufraneb, cymoxanil, cyproconazole, cyprofuram, dichlorophen, diclobutrazol, diclofluanide, diclomezine, dicloran, diethofencarb, difenoconazole, dimethirimol, dimethomorph, diniconazole, dinocap, diphenylamine, dipyrithione, ditalimfos, dithianone, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachloro benzene, hexaconazole, hymexazole, imazalil, imibenconazole, iminoctadine, iprobenfos (IBP), iprodione, isoprothiolane, kasugamycin, copper preparations such as: copper hydroxide, copper napthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxine, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, toiclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furan-carboxylic acid, oxytetracycline, probenazole, streptromycin, tecloftalam, copper sulphate and other copper preparations.

Insecticides/acaricides/nematicides:

abamectin, abarnectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis,* bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chloethoxyfos, chloetoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinone, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoate, oxamyl, oxydemethon M, oxydeprofos, parathion A, parathion M, pennethrin, phenthoate, phorate, phosalone, phosmet, phosphamdon, phoxim, pirimicarb, pirimiphos M,, primiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum, pyridaben, pyrimidifen, pyriproxifen, quinalphos,

RH 5992, salithion, sebufos, silafluofen, sulfotep, suiprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

It is also possible to have a mixture with other known active substances such as herbicides or with fertilizers and growth regulators.

The active substances can be used as such, in the form of their formulations or the use forms prepared therefrom, such as ready-to-use solutions, suspensions, wettable powders, pastes, soluble powders, dusting preparations and granules. They are used in the customary manner, for example by watering, spraying, atomizing, scattering, dusting, foaming, brushing on and the like. It is furthermore possible to apply the active substances by the ultra low volume method or to inject the active substance preparation or the active substance itself into the soil. The seeds of the plants can also be treated.

In the treatment of parts of plants, the active substance concentrations in the use forms can be varied in a relatively wide range: they are in general between 1 and 0.0001% by weight, preferably between 0.5 and 0.001% by weight.

The amounts of active substance generally required for treating seeds are from 0.001 to 50 g per kilogram of seeds, preferably 0.01 to 10 g.

The concentrations of active substance required for treating the soil are from 0.00001 to 0.1% by weight, preferably from 0.0001 to 0.02% by weight, at the site of action.

PREPARATION EXAMPLES

Example 1

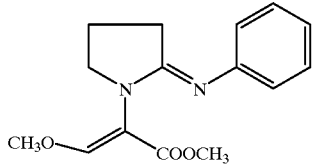

(Process a)

4.5 g (50 mmol) of aniline were introduced into 100 ml of toluene, 7.5 g (60 mmol) of phosphorus oxychloride in 30 ml of toluene were added dropwise, 10.0 g (50 mmol) of N-(methoxycarbonyl-methoxymethylidene)-methyl-2-pyrrolidone (Example II-1) in 50 ml of toluene were added, and the mixture was heated at 80° C. for 4 hours.

The reaction mixture was then poured into 300 ml of water, made alkaline with potassium carbonate solution and extracted twice with 100 ml of ether each time, and the combined organic extracts were dried over sodium sulphate and concentrated in vacuo. Trituration with a mixture of 10 ml of ether and 10 ml of n-pentane resulted in a yellow solid.

4.0 g (29% of theory) of N-(methoxycarbonyl-methoxymethylidene)-methyl-2-phenyliminopyrrolidine of melting point 70 to 74° C. are obtained.

$^1$H-NMR (CDCl$_3$): δ=2.00–2.07 (m, 2H, CH$_2$), 2.40 (t, 2H, CH$_2$), 3.50 (t, 2H, CH$_2$), 3.75 (s, 3H, OCH$_3$), 3.92 (s, 3H, OCH$_3$), 6.78–7.30 (m, 5H, Ar—H), 7.37 (s, 1H, —CH=).

Example 2

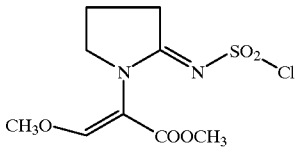

(Process b)

4.0 g (20 mmol) of N-(methoxycarbonyl-methoxymethylidene)-methyl-2-pyrrolidinone (Example II-1) were introduced into 40 ml of chloroform, 2.8 g (20 mmol) of chlorosulphonyl isocyanate were added dropwise, and the mixture was heated under reflux for 3 hours. It was then dried and concentrated. The residue was subsequently stirred in 25 ml of ether, and the resulting precipitate was filtered off and dried.

3.1 g (52% of theory) of N-(methoxycarbonyl-methoxymethylidene)-methyl-2-chlorosulphonyliminopyrrolidine are obtained.

$^1$H-NMR (CDCl$_3$): δ=2.29–2.37 (m, 2H, CH$_2$), 2.37 (t, 2H, CH$_2$), 3.57–3.79 (m, 3H, CH$_2$, NH), 3.77 (s, 3H, OCH$_3$), 3.97 (s, 3H, OCH$_3$), 7.45 (s, 1H, —CH=).

Example 3

(Process d)

2.4 g (80 mmol) of 80% sodium hydrode were introduced into 150 ml of dimethyl formamide and, at 5–10° C., 12.1 g (40 mmol) of N-methoxycarbonylmethyl-2-(2,6-dichlorophenyl)-imino-oxazolidine (Example VII-1) in 60.0 g (1 mol) of methyl formate were added dropwise, and the mixture was stirred at room temperature for 18 hours.

The reaction mixture was poured into 250 ml of water, acidified with dilute hydrochloric acid, extracted 3 times with 200 ml of methylene chloride each time, dried over sodium sulphate and concentrated in vacuo.

The residue was then taken up in 150 ml of dimethylformamide, 10.8 g (80 mmol) of potassium carbonate were added, the mixture was stirred at room temperature for 30 minutes, 6.2 g (50 mmol) of dimethyl sulphate were added dropwise, and the mixture was stirred at room temperature for 18 hours.

The suspension was subsequently poured into 600 ml of water and extracted 3 times with 200 ml of methylene chloride each time, and the combined extracts were dried over sodium sulphate and concentrated in vacuo. Silica gel was then chromatographed with ether.

1.6 g (8% of theory) of N-(methoxycarbonyl-methoxymethylidene)-methyl-2-(2,6-dichlorophenyl)-imino-oxazolidine are obtained.

$^1$H-NMR (CDCl$_3$): δ=3.79 (s, 3H, OCH$_3$), 3.80 (t, 2H, CH$_2$), 3.98 (s, 3H, OCH$_3$), 4.46 (t, 2H, CH$_2$), 6.82 (t, 1H, Ar—H), 7.25 (d, 2H, Ar—H), 7.51 (s, 1H, —CH=).

Compounds of the formula (I) listed in Table 1 below can be prepared, for example, in analogy to the preparation examples and in accordance with the general descriptions of the processes according to the invention:

TABLE 1

| Ex. No. | B | A | X | Y | Z | R | Physical data |
|---|---|---|---|---|---|---|---|
| 4 | CH$_2$ | CH$_2$ | CH$_3$OCH= | —COOCH$_3$— | — | 2-Cl-phenyl | m.p. 80–84° C. |
| 5 | CH$_2$ | CH$_2$ | CH$_3$OCH= | —COOCH$_3$— | — | 2,4-Cl$_2$-phenyl | $^1$H-NMR (CDCl$_3$): δ = 2.02–2.11(m, 2H, CH$_2$), 2.33(t, 2H, CH$_2$), 3.55(t, 2H, CH$_2$), 3.75(s, 3H, OCH$_3$), 6.76–6.80(m, 1H, Ar—H), 7.05–7.08(m, 1H, Ar—H), 7.42(s, 1H, —CH=). |

TABLE 1-continued

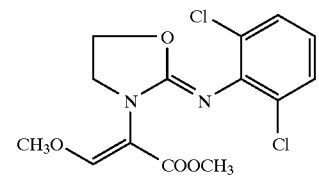

| Ex. No. | B | A | X | Y | Z | R | Physical data |
|---|---|---|---|---|---|---|---|
| 6 | CH₂ | CH₂ | CH₃OCH= | —COOCH₃— | — | 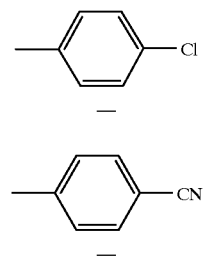 | m.p. 92–94° C. |
| 7 | CH₂ | CH₂ | CH₃OCH= | —COOCH₃— | — | 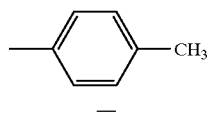 | ¹H-NMR (CDCl₃): δ = 2.06–2.15(m, 2H, CH₂), 2.47(t, 2H, CH₂), 3.58(t, 2H, CH₂), 3.78(s, 3H, OCH₃), 3.96(s, 3H, OCH₃), 6.87–6.99(m, 2H, Ar—H), 7.35–7.51(m, 3H, Ar—H, —CH=). |
| 8 | CH₂ | CH₂ | CH₃OCH= | —COOCH₃— | — | 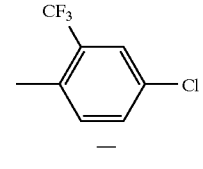 | m.p. 60–64° C. |
| 9 | CH₂ | O | CH₃OCH= | —COOCH₃— | — | 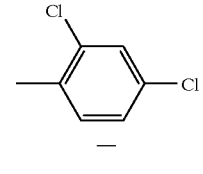 | ¹H-NMR (CDCl₃): δ = 3.77(s, 3H, OCH₃), 3.78(t, 2H, OCH₃), 4.46(t, 2H, CH₂), 7.03–7.58(m, 1H, Ar—H), 7.22–7.32(m, 2H, Ar—H), 7.47–7.49(m, 2H, Ar—H, —CH=). |
| 10 | CH₂ | O | CH₃OCH= | —COOCH₃— | — | 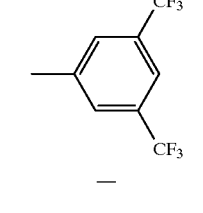 | m.p. 40–44° C. |
| 11 | CH₂ | O | CH₃OCH= | —COOCH₃— | — | 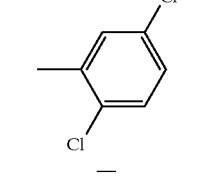 | m.p. 133–36° C. |
| 12 | CH₂ | O | CH₃OCH= | —COOCH₃ | — | 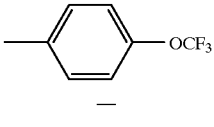 | ¹H-NMR (DMSO): δ = 3.68 |
| 13 | CH₂ | O | CH₃OCH= | —COOCH₃ | — |  | ¹H-NMR (CDCl₃): δ = 3.76 |

TABLE 1-continued

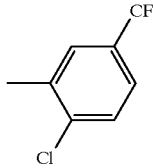

| Ex. No. | B | A | X | Y | Z | R | Physical data |
|---|---|---|---|---|---|---|---|
| 14 | CH$_2$ | O | CH$_3$OCH= | —COOCH$_3$ | — | 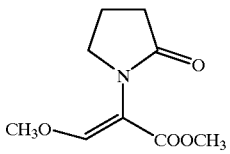 | $^1$H-NMR (CDCl$_3$): δ = 3.78 |
| 15 | CH$_2$ | S | CH$_3$OCH= | —COOCH$_3$ | — |  | H-NMR (CDCl$_3$): δ = 2.11 |

Preparation of the starting materials of the Formula (II)

Example (II-1)

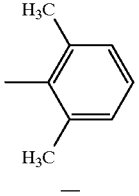

3.0 g (0.1 mol) of 80% sodium hydride were introduced into 150 ml of dimethylformamide and, at 5–10° C., 7.9 g (0.05 mol) of N-methoxycarbonylmethyl-2-pyrrolidinone (Example XVII-1) in 72.0 g (1.2 mol) of methyl formate were added dropwise, and the mixture was stirred at room temperature for 16 hours.

It was then added to 100 ml of water while cooling, the mixture was extracted 3 times with 50 ml of ether each time, the ether extracts were discarded, the aqueous phase was acidified with dilute hydrochloric acid, extracted 3 times with 50 ml of ethyl acetate each time, dried over sodium sulphate and concentrated in vacuo.

The residue was then taken up in 100 ml of dimethylformamide, 9.5 g (0.07 mol) of potassium carbonate were added, the mixture was stirred at room temperature for 20 minutes, 6.3 g (0.05 mol) of dimethyl sulphate were added dropwise, and the mixture was stirred at room temperature for 19 hours.

The suspension was subsequently poured into 600 ml of water and extracted 3 times with 200 ml of ether each time, the water phase was acidified with dilute hydrochloric acid and extracted 3 times with 200 ml of methylene chloride each time, and the combined extracts were dried over sodium sulphate and concentrated in vacuo. Subsequent stirring with ether resulted in a yellow solid.

2.6 g (26% of theory) of N-(methoxycarbonyl-methoxymethylidene)-methyl-2-pyrrolidinone of melting range 57 to 60° C. are obtained.

$^1$H-NMR (CDCl$_3$): δ=2.09–2.19 (m 2H, CH$_2$), 2.45 (t, 2H, CH$_2$), 3.52 (t, 2H, CH$_2$), 3.73 (s, 3H, OCH$_3$), 3.91 (s, 3H, OCH$_3$), 7.42 (s, 1H, —CH=).

Preparation of the precursor (XVII-1)

1.5 g (50 mmol) of 80% sodium hydride were introduced into 60 ml of anhydrous tetrahydrofuran, 4.3 g (50 mmol) of 2-pyrrolidinone in 40 ml of anhydrous tetrahydrofuran were added dropwise, the mixture was stirred at room temperature for 20 minutes, 9.1 g (60 mmol) of methyl bromoacetate were added dropwise, and the mixture was stirred at room temperature for a further 2 hours.

The suspension was then poured into 100 ml of water and extracted 3 times with ethyl acetate each time, and the organic extracts were dried and concentrated.

3.7 g (47% of theory) of N-methoxycarbonylmethyl-2-pyrrolidinone are obtained.

$^1$H-NMR (CDCl$_3$): δ=2.07–2.13 (m 2H, CH$_2$), 2.44 (t, 2H, CH$_2$), 3.49 (t, 2H, CH$_2$), 3.74 (s, 3H, OCH$_3$), 4.08 (s, 2H, CH$_2$CO).

Example (II-2)

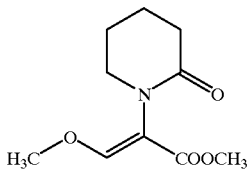

48.0 g (1.6 mol) of 80% sodium hydride were introduced into 600 ml of dimethyl formamide and, at 5–10° C., 140 g (0.8 mol) of N-methoxycarbonylmethyl-2-piperidinone (Example XVII-2) in 960.0 g (16 mol) of methyl formate were added dropwise, and the mixture was stirred at room temperature for 16 hours.

It was then added to 2 l of water while cooling, the mixture was extracted 3 times with 300 ml of ether each time, the ether extracts were discarded, the aqueous phase was acidified with dilute hydrochloric acid, extracted 3 times with 300 ml of methylene chloride each time, dried over sodium sulphate and concentrated in vacuo.

The residue was then taken up in 700 ml of dimethylformamide, 138.0 g (1 mol) of potassium carbonate were added, the mixture was stirred at room temperature for 30 minutes, 104.0 g (0.8 mol) of dimethyl sulphate were added dropwise while cooling, and the mixture was stirred at room temperature for 18 hours.

The suspension was subsequently poured into 2 l of water, acidified with dilute hydrochloric acid and extracted 4 times with 300 ml of methylene chloride each time, and the combined extracts were dried over sodium sulphate and concentrated in vacuo. The residue was subsequently chromatographed on basic aluminium oxide (active. IV) with ether/ethyl acetate.

2.7 g (2% of theory) of N-(methoxycarbonyl-methoxymethylidene)-methyl-2-piperidinone are obtained.

$^1$H-NMR (CDCl$_3$): $\delta$=1.79–1.83 (m 4H, CH$_2$—CH$_2$), 2.43–2.44 (m, 2H, CH$_2$), 3.67 (s, 3H, OCH$_3$), 3.43–3.48 (m, 2H, CH$_2$), 3.46 (s, 3H, OCH$_3$), 4.88 (d, 1H, CH), 5.21 (d, 1H, CH).

Preparation of the precursor (XVII-2)

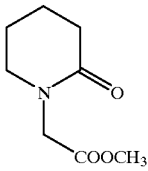

3.0 g (0.1 mol) of 80% sodium hydride were introduced into 70 ml of anhydrous tetrahydrofuran, 10.9 g (0.11 mol) of valerolactam in 30 ml of anhydrous tetrahydrofuran were added dropwise, the mixture was stirred at room temperature for 30 minutes, 16.7 g (0.11 mmol) of methyl bromoacetate were added dropwise and the mixture was stirred at room temperature for a further 20 hours.

The suspension was then poured into 200 ml of water and extracted 3 times with 40 ml of ethyl acetate each time, and the organic extracts were dried and concentrated.

12.4 g (72% of theory) of N-methoxycarbonylmethyl-2-piperidinone are obtained.

$^1$H-NMR (CDCl$_3$): $\delta$=1.85–1.89 (m 4H, CH$_2$—CH$_2$), 2.40–2.44 (m, 2H, CH$_2$), 3.36–3.95 (m, 2H, CH$_2$), 3.73 (s, 3H, OCH$_3$), 4.12 (s, 2H, CH$_2$CO).

Example (II-3)

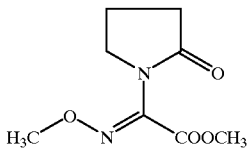

92.3 g (0.825 mol) of potassium tert-butoxide were introduced into 700 ml of tert-butanol and, at 30° C., 117 g (0.75 mol) of N-methoxycarbonylmethyl-2-pyrrolidinone (Example XVII-1) in 255 g (2.55 mol) of 90% tert-butyl nitrile were added, the mixture was stirred at 60° C. for 1 hour, 160.5 g (1.125 mol) of methyl iodide were added at room temperature, and the mixture was stirred at room temperature for 20 hours.

The suspension was subsequently concentrated in vacuo, the residue was partitioned between 400 ml of methylene chloride and 300 ml of water, the aqueous phase was extracted twice with 100 ml of methylene chloride each time, and the organic extracts were dried and concentrated in vacuo.

Crude yield: 107 g (red oil)

Chromatography on silica gel with ether as mobile phase results in 18.6 g (12% of theory) of N-(methoxycarbonyl-methoximino)-methyl-2-pyrrolidinone of melting range: 67–71° C.

$^1$H-NMR (CDCl$_3$): $\delta$=2.81–2.23 (m 2H, CH$_2$), 2.44 (t, 2H, CH$_2$), 3.79 (t, 2H, CH$_2$), 3.88 (s, 3H, OCH$_3$), 4.05 (s, 3H, OCH$_3$).

Example (II-4)

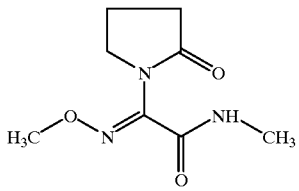

9.3 g (0.3 mol) of methylamino were introduced into 100 ml of methanol and, at room temperature, 14.0 g (0.07 mol) of N-(methoxycarbonyl-methoximino)-methyl-2-pyrrolidinone (Example II-3) in 20 ml of methanol were added dropwise, and the mixture was left to stand at room temperature for 48 hours.

The solution was then concentrated in vacuo, the residue was partitioned between 200 ml of chloroform and 100 ml of water, and the organic phase was dried over sodium sulphate and concentrated in vacuo. The residue was subsequently stirred in 20 ml of ether/10 ml of petroleum ether and the precipitate was filtered off and dried.

5.8 g (42% of theory) of N-(methylcarbamoyl-methoxyimino)-methyl-2-pyrrolidinone of melting range 60–63° C. are obtained.

$^1$H-NMR (CDCl$_3$): $\delta$=2.18–2.25 (m 2H, CH$_2$), 2.45 (t, 2H, CH$_2$), 2.90 (d, 3H, NCH$_3$), 3.75 (t, 2H, CH$_2$), 3.97 (s, 3H, OCH$_3$), 6.58 (br. s, 1H, NH).

Example (II-5)

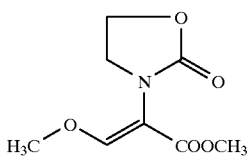

48.0 g (1.6 mol) of 80% sodium hydride were introduced into 600 ml of dimethylformamide and, at 5–10° C., 127.0 g (0.8 mol) of N-methoxycarbonylmethyl-2-oxazoliidinone (Example XVII-3) in 720.0 g (12 mol) of methylformate were added dropwise, and the mixture was stirred at room temperature for 18 hours.

The reaction mixture was poured into 3 l of water and extracted 3 times with 500 ml of ether each time, the ether extracts were discarded, the aqueous phase was acidified with dilute hydrochloric acid and extracted 4 times with 500 ml of methylene chloride each time, and the organic phase was dried over sodium sulphate and concentrated in vacuo.

The residue was then taken up in 600 ml of dimethylformamide, 138.0 g (1.0 mol) of potassium carbonate were added, the mixture was stirred at room temperature for 30 minutes, 104.0 g (0.8 mol) of dimethyl sulphate were added dropwise, and the mixture was stirred at room temperature for 18 hours.

The suspension was subsequently poured into 1.5 l of water, acidified with dilute hydrochloric acid and extracted 4 times with 500 ml of methylene chloride each time, and the combined extracts were dried over sodium sulphate and concentrated in vacuo. Stirring with ether was then carried out.

97.0 g (56% of theory) of N-(methoxycarbonyl-methoxymethylidene)-methyl-2-oxazolidinone of melting range 35 to 40° C. are obtained.

$^1$H-NMR (CDCl$_3$): δ=3.74 (t, 2H, CH$_2$), 3.76 (s, 3H, OCH$_3$), 3.95 (s, 3H, OCH$_3$), 4.45 (t, 2H, CH$_2$), 7.46 (s, 1H, —CH=).

Preparation of the precursor (XVII-3)

3.0 g (0.1 mol) of 80% sodium hydride were introduced into 100 ml of absolute tetrahydrofuran, 9.6 g (0.11 mol) of 2-oxazolidinone in 30 ml of absolute tetrahydrofuran were added dropwise, the mixture was stirred at room temperature for 2 hours, 16.7 g (0.11 mol) of methyl bromoacetate were added dropwise, and the mixture was stirred at room temperature for a further 18 hours.

The suspension was then poured into 100 ml of water and extracted 3 times with 70 ml of methylene chloride each time, and the organic extracts were dried and concentrated.

12.3 g (77% of theory) of N-methoxycarbonylmethyl-2-oxyzolidinone are obtained.

$^1$H-NMR (CDCl$_3$): δ=3.72 (t, 2H, CH$_2$), 3.77 (s, 3H, OCH$_3$), 4.05 (s, 2H, CH$_2$CO), 4.40 (t, 2H, CH$_2$).

The starting compounds of the formula (II) which are listed in Table 2 below can be prepared for example in analogy to the preparation examples and in accordance with the general descriptions:

TABLE 2

| Ex. No. | B | A | X | Y | Physical data |
|---|---|---|---|---|---|
| II-6 | CH$_2$ | CH$_2$ | CH$_3$ON= | —COOC(CH$_3$)$_3$ | $^1$H-NMR (CDCl$_3$): δ = 1.53(s, 9H); 2.18–2.23(m, 2H); 2.44(t, 2H); 3.79 (t, 2H); 3.88(s, 3H); 4.04(s, 3H) |

Preparation of the starting materials of the formula (V)

Example (V-1)

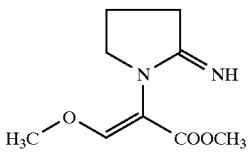

20.0 g (80 mmol) of N-(methoxycarbonyl-methoxyethylidene)-methyl-2-pyrrolidinone (Example II-1) were introduced into 160 ml of chloroform, 11.2 g (80 mmol) of chlorosulphonyl isocyanate were added dropwise, and the mixture was heated under reflux for 3 hours. Then, at room temperature, the pH was adjusted to 10 with 30% strength sodium hydroxide solution, the mixture was stirred at room temper for 2 hours, the phases were separated and the organic phase was dried and concentrated.

12.1 g (76% of theory) of N-(methoxycarbonyl-methoxymethylidene)-methyl-2-imino-2-pyrrolidine are obtained.

$^1$H-NMR (CDCl$_3$): δ=2.08–2.18 (m, 2H, CH$_2$), 2.45 (t, 2H, CH$_2$), 3.54 (t, 2H, CH$_2$), 3.73 (s, 3H, OCH$_3$), 3.90 (s, 3H, OCH$_3$), 5.00–5.15 (br. s,, 1H, NH), 7.42 (s, 1H, —CH=).

Preparation of the starting materials of the formula (VII)

Example (VII-1)

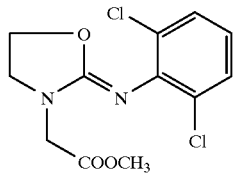

23.1 g (0.1 mol) of 2-(2,6-dichlorophenyl)-imino-oxazolidine (compare DE-OS (German Published Specification) 19 63 192) were introduced into 150 ml of tetrahydrofuran, 13.4 g (0.12 mol) of potassium tert-butoxide were added, the mixture was stirred at room temperature for 30 minutes, then 21.8 g (0.14 ml) of methyl bromoacetate were added and the mixture was stirred at room temperature for 5 hours.

The suspension was subsequently poured into 500 ml of water and extracted 3 times with 80 ml of methylene chloride each time, and the organic phase was dried over sodium sulphate and concentrated in vacuo. Chromatography on silica gel with ether as mobile phase then provided a colourless oil.

16.9 g (56% of theory) of N-methoxycarbonylmethyl-2-(2,6-dichlorophenyl)-imino-oxazolidine are obtained.

$^1$H-NMR (CDCl$_3$): δ=3.76 (t, 2H, CH$_2$), 3.79 (s, 3H, OCH$_3$), 4.23 (s, 2H, CH$_2$CO), 4.38 (t, 2H, CH$_2$), 6.84 (t, 1H, Ar—H), 7.23 (d, 2H, Ar—H).

The compounds of the formula (VII) listed in Table 3 below can be prepared for example in analogy to the preparation example and in accordance with the general description:

TABLE 3

(VII)

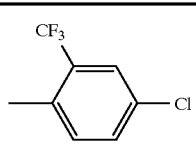

| Ex. No. | B | A | Y$^1$ | Z | R | Physical data |
|---|---|---|---|---|---|---|
| VII-2 | CH$_2$ | O | —COOCH$_3$— | — | 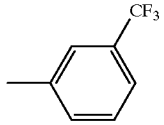 | m.p. 35–38° C. |
| VII-3 | CH$_2$ | O | —COOCH$_3$— | — | 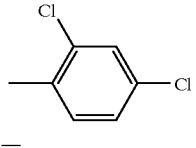 | $^1$H-NMR (CDCl$_3$): δ = 3.69 (t, 2H, CH$_2$), 3.77 (s, 3H, OCH$_3$), 4.18 (s, 2H, CH$_2$CO), 4.41 (t, 2H, CH$_2$), 7.18–7.34 (m, 4H, Ar—H). |
| VII-4 | CH$_2$ | O | —COOCH$_3$— | — | 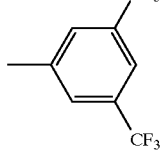 | $^1$H-NMR (CDCl$_3$): δ = 3.73 (t, 2H, CH$_2$), 3.78 (s, 3H, OCH$_3$), 4.20 (s, 2H, CH$_2$CO), 4.40 (t, 2H, CH$_2$), 7.01–7.36 (m, 3H, Ar—H). |
| VII-5 | CH$_2$ | O | —COOCH$_3$— | — | 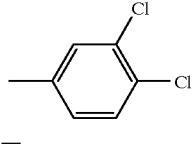 | m.p. 47–51° C. |
| VII-6 | CH$_2$ | O | —COOCH$_3$— | — | 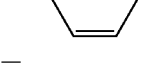 | $^1$H-NMR (CDCl$_3$): δ = 3.68 (t, 2H, CH$_2$), 3.77 (s, 3H, OCH$_3$), 4.15 (s, 2H, CH$_2$CO), 4.40 (t, 2H, CH$_2$), 6.84–6.90 (m, 1H, Ar—H), 7.17–7.40 (m, 1H, Ar—H). |
| VII-7 | CH$_2$ | CH$_2$ | —COOCH$_3$ | — | | $^1$H-NMR (CDCl$_3$): δ = 1.97 |

TABLE 3-continued (VII)

| Ex. No. | B | A | Y¹ | Z | R | Physical data |
|---|---|---|---|---|---|---|
| VII-8 | CH₂ | O | —COOCH₃ | — | 3-Cl-4-(CF₃)-phenyl | ¹H-NMR (CDCl₃): δ = 3.74 |
| VII-9 | CH₂ | O | —COOCH₃ | — | 4-OCF₃-phenyl | ¹HNMR (CDCl₃): δ = 3.67 |
| VII-10 | CH₂ | S | —COOCH₃ | — | 2,6-dimethylphenyl | ¹H-NMR (CDCl₃): δ = 2.09 |
| VII-11 | CH₂ | O | —COOCH₃ | — | 2,5-dichlorophenyl | ¹H-NMR (CDCl₃): δ = 3.69 |
| VII-12 | CH₂ | S | —COOCH₃ | —N=CH— | 4-Cl-phenyl | ¹³C-NMR (DMSO): δ = 26.45 |

Preparation of the starting materials of the formula (VIII)

Example (VIII-1)

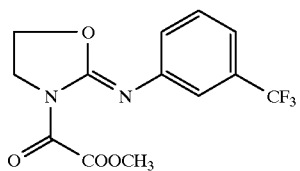

5.8 g (25 mmol) of 2-(3-trifluoromethylphenyl)-iminooxazolidine (compare, for example, DE-OS (German Published Specification) 19 63 192) were introduced into 60 ml of tetrahydrofuran, 5.5 g (40 mmol) of potassium carbonate were added, 3.6 g (30 mmol) of methyl oxalyl chloride in 40 ml of tetrahydrofuran were added dropwise at 0° C., and the mixture was stirred at room temperature for 72 h.

The suspension was then added to 250 ml of water and extracted 3 times with 70 ml of ethyl acetate each time, and the organic extracts were dried over sodium sulphate and concentrated in vacuo. The residue was subsequently stirred in 30 ml of n-pentane, and the resulting solid was filtered off and dried.

2.1 g (26% of theory) of the abovementioned compound, which decomposes on heating to 80° C., are obtained.

¹H-NMR (CDCl₃): δ=3.36 (s, 3H, OCH₃), 3.83 (t, 2H, CH₂), 3.97 (t, 2H, CH₂), 7.74–7.90 (m, 4H, Ar—H).

USE EXAMPLES

Example A

Podosphaera test (apple)/protective
Solvent: 4.7 parts by weight of acetone

Emulsifier: 0.3 part by weight of alkyl-aryl-polyglycol ether

To prepare an expedient active substance preparation, 1 part by weight of active substance is mixed with the stated amounts of solvent and emulsifier, and the concentrate is diluted with water to the required concentration.

To test for protective activity, young plants are sprayed with an active substance preparation until dripping wet. After the spray deposit has dried on, the plants are inoculated with conidia of *Podosphaera leucotricha,* which is the cause of apple mildew.

The plants are then placed in a glass house at 23 and at a relative humidity of about 70%.

Evaluation takes place 10 days after the inoculation.

In this test, for example the compound of Preparation Example 9 shows an efficacy of 86% at an active substance concentration of 10 ppm.

We claim:

1. Compounds of the formula (I),

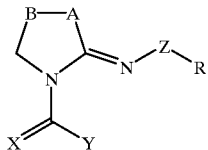

(I)

in which

A represents oxygen or sulphur,

B represents the $CH_2$ group,

X represents the groups $=CHR^1$ or $=NR^2$, where $R^1$ represents alkyl, alkoxy, alkylthio, alkylamino and dialkylamino, which is in each case optionally substituted by halogen, cyano or $C_1$–$C_4$-alkoxy and has in each case 1 to 4 carbon atoms in the alkyl radicals, and $R^2$ represents amino or represents alkyl, alkoxy, alkylamino and dialkylamino, which is in each case optionally substituted by halogen, cyano or $C_1$–$C_4$-alkoxy and has in each case 1 to 4 carbon atoms in the alkyl radicals, Y represents the groups —CO—$C_1$–$C_4$-alkyl, —CO—O—$C_1$–$C_4$-alkyl, —CO—NH—$C_1$–$C_4$-alkyl, —CO—N($C_1$–$C_4$-alkyl)$_2$, —CO—NR$^3$—OR$^4$ and

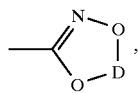

where $R^3$ represents hydrogen or $C_1$–$C_4$-alkyl, $R^4$ represents hydrogen, represents alkyl or alkenyl, which is in each case optionally substituted by halogen, $C_1$–$C_4$-alkoxy-$C_1$–$C_4$-alkoxy, N,N-di-($C_1$–$C_4$-alkyl)-amino, N-($C_1$–$C_4$-alkylcarbonyl)-amino, N-($C_1$–$C_4$-alkyl)-N-($C_1$–$C_4$-alkylcarbonylamino; N-($C_1$–$C_4$)-alkoxy-carbonyl)-amino or N-($C_1$–$C_4$-alkyl)-N-($C_1$–$C_4$)-alkoxy-carbonyl)-amino and has in each case 1 to 8 carbon atoms, represents $C_1$–$C_4$-alkoxy-carbonyl, represents $C_1$–$C_4$-alkylamino-carbonyl or represents di-($C_1$–$C_4$-alkyl)-aminocarbonyl; and D represents alkanediyl which is optionally substituted by halogen, $C_1$–$C_4$-alkyl or halogeno-$C_1$–$C_4$-alkyl and has 1 to 3 carbon atoms, Z represents a direct linkage; represents $C_1$–$C_8$-alkylene, $C_2$–$C_8$-alkenylene and $C_2$–$C_8$-alkinylene, which is in each case optionally substituted by halogen, $C_1$–$C_4$-alkyl, halogeno-$C_1$–$C_4$-alkyl, nitro, cyano, $C_1$–$C_4$-alkoxy, halogeno-$C_1$–$C_4$-alkoxy, $C_1$–$C_4$-alkylthio and/or $C_1$–$C_4$-halogenoalkylthio; and represents the groups —$(CHR^5)_n$—O—, —$(CHR^5)_n$—S—, —$(CHR^5)_n$—NH—, —$(CHR^5)_n$—NR$^6$—, —$(CHR^5)_n$—SO—, —$(CHR^5)_n$—SO$_2$—, —$(CHR^5)_n$—O—SO—, —$(CHR^5)_n$—SO—O$_2$—, —$(CHR^5)_n$—O—SO$_2$—, —$(CHR^5)_n$—SO$_2$—O—, —$(CHR^5)_n$—CO—, —$(CHR^5)_n$—CO—O—, —$(CHR^5)_n$—O—CO—, —$(CHR^5)_n$—CR$^6$=N—O—, —$(CHR^5)_n$—CR$^6$=N—N—CR$^7$—, —$(CHR^5)_n$—N=CR$^7$—, —$(CHR^5)_n$—O—N=CR$^7$—, where n represents the numbers 0, 1, 2, 3 or 4, where the radicals $R^5$ can be different when n is greater than 1; and $R^5$, $R^6$ and $R^7$ independently of one another represent hydrogen and represent $C_1$–$C_8$-alkyl, $C_2$–$C_8$-alkenyl, $C_2$–$C_8$-alkinyl or phenyl, which is in each case optionally substituted by halogen, $C_1$–$C_4$-alkyl, halogeno-$C_1$–$C_4$-alkyl, nitro, cyano, $C_1$–$C_4$-alkoxy, halogeno-$C_1$–$C_4$-alkoxy, $C_1$–$C_4$-alkylthio and/or $C_1$–$C_4$-halogenoalkylthio, R represents hydrogen; halogen; represents $C_1$–$C_8$-alkyl, $C_2$–$C_8$-alkenyl or $C_2$–$C_8$-alkinyl, which is in each case optionally substituted by halogen, halogeno-$C_1$–$C_4$-alkyl, nitro, cyano, $C_1$–$C_4$-alkoxy, halogeno-$C_1$–$C_4$-alkoxy, $C_1$–$C_4$-alkylthio and/or $C_1$–$C_4$-halogenoalkylthio; and represents in each case optionally mono- to pentasubstituted, identically or differently, cycloalkyl with 3 to 7 carbon atoms, cycloalkenyl with 5 to 7 carbon atoms, aryl with 6 to 10 carbon atoms, (optionally benzo-fused) heterocyclyl (saturated or partially unsaturated) with 3 to 7 ring members, of which 1 to 3 represent N, O, and/or S atoms, and (optionally benzo-fused) heteroaryl with 5 or 6 ring members, of which one represents oxygen, sulphur or nitrogen and optionally one or two others represent nitrogen, where the substituents are in each case selected from the following list: oxygen (as replacement for two geminal hydrogen atoms), halogen, cyano, nitro, amino, hydroxyl, formyl, carboxyl, carbamoyl, thiocarbamoyl, in each case straight-chain or branched alkyl, alkoxy, alkylthio, alkylsulphinyl or alkylsulphonyl with in each case 1 to 6 carbon atoms, in each case straight-chain or branched alkenyl or alkenyloxy with in each case 2 to 6 carbon atoms, in each case straight-chain or branched halogenoalkyl, halogenoalkoxy, halogenoalkylthio, halogenoalkyl-sulphinyl or halogenoalkylsulphonyl with in each case 1 to 6 carbon atoms and 1 to 13 identical or different halogen atoms, in each case straight-chain or branched halogenoalkenyl or halogenoalkenyloxy with in each case 2 to 6 carbon atoms and 1 to 13 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl with in each case 1 to 6 carbon atoms in the individual alkyl moieties, in each case optionally mono- or polysubstituted, identically or differently by halogen and/or straight-chain or branched alkyl with 1 to 4 carbon atoms and/or straight-chain or branched halogenoalkyl with 1 to 4 carbon atoms and 1 to 9 identical or different halogen atoms, and in each case doubly linked alkylene or dioxyalkylene with in each case 1 to 6 carbon atoms, cycloalkyl with 3 to 6 carbon atoms, heterocyclyl or heterocyclyl-methyl with in each case 3 to 7 ring members, of which in each case 1 to 3 are identical or different nitrogen, oxygen and/or sulphur atoms, and phenyl, phenoxy, benzyl, benzyloxy, phenylethyl or phenylethyloxy, which is in each case optionally mono- or polysubstituted in the phenyl moiety, identically or differently by halogen, cyano and/or straight-chain or branched alkyl with 1 to 4 carbon atoms and/or straight-chain or branched halogenoalkyl with 1 to 4 carbon atoms and 1 to 9 identical or different halogen atoms and/or straight-chain or branched alkoxy with 1 to 4 carbon atoms and/or straight-chain or branched halogenoalkoxy with 1 to 4 carbon atoms and 1 to 9 identical or different halogen atoms.

2. Compounds of the formula (I) according to claim 1, in which

A represents oxygen or sulphur,

B represents the $CH_2$ group,

X represents the groups $=CHR^1$ or $=NR^2$, where $R^1$ represents methyl, ethyl, propyl, methoxy, ethoxy, methylthio, ethylthio, methylamino, ethylamino or dimethylamino, which is in each case optionally substituted by fluorine, chlorine, cyano, methoxy or ethoxy, $R^2$ represents amino or represents methyl, ethyl, methoxy, ethoxy, methylamino, ethylamino or dimethylamino, which is in each case optionally substituted by fluorine, chlorine, cyano, methoxy or ethoxy, Y represents the groups —$COCH_3$, —$COC_2H_5$, —$COC_3H_7$—n, —$COC_3H_7$—i, —$COOCH_3$, —$COOC_2H_5$, —$COOC_3H_7$—n, —$COOC_3H_7$—i, —CO—$NHCH_3$, —CO—$NHC_2H_5$, —CO—$NHC_3H_7$—n, —CO—$NHC_3H_7$—i, —CO—N($CH_3$), —CO—N($CH_3$)$C_2H_5$, —CO—N($C_2H_5$)$_2$, —CO—N($CH_3$)$C_3H_7$—n, —CO—N($CH_3$)$C_3H_7$—i, —CO—$NR^3$—$OR^4$ and

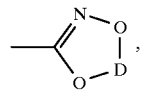, where $R^3$ represents hydrogen, methyl, ethyl, n- or i-propyl, and $R^4$ represents hydrogen, represents methyl, ethyl, n- or i-propyl, n-, i-, s- or t-butyl, which is in each case optionally substituted by fluorine, chlorine, methoxy, ethoxy, n- or i-propoxy, methoxy-ethoxy, ethoxy-ethoxy, dimethylamino, diethylamino, acetylamino, propionylamino, N-methyl-acetylamino, N-ethylacetylamino, N-methyl-propionylamino, N-ethylpropionylamino, methoxycarbonylamino, ethoxycarbonylamino, N-methyl-N-methoxycarbonylamino, N-ethyl-N-methoxycarbonylamino, N-methyl-N-ethoxycarbonylamino or N-ethyl-N-ethoxycarbonylamino, represents methoxycarbonyl, ethoxycarbonyl, methylaminocarbonyl, ethylaminocarbonyl, dimethylaminocarbonyl or diethylaminocarbonyl; and D represents methylene or ethane-1,2-diyl, which is in each case optionally substituted by fluorine, chlorine, methyl, ethyl or trifluoromethyl, Z represents a direct linkage; represents —$CH_2$—, —$CH_2CH_2$—, —CH=CH—, —$CH_2O$—, —$CH_2S$—, —$CH_2NH$—, —$CH_2N(CH_3)$—, —N=CH—, —N=C($CH_3$)— and —N=C(CN)—, which is in each case optionally substituted by fluorine, chlorine, methyl, ethyl or trifluoromethyl, R represents hydrogen; represents chlorine or bromine; represents methyl, ethyl and ethenyl, which is in each case optionally substituted by fluorine, chlorine or trifluoromethyl;

represents cyclopropyl, cyclobutyl, cyclopentyl, cyclohexyl, cyclopentenyl or cyclohexenyl, which is in each case optionally mono- to trisubstituted, identically or differently, by fluorine, chlorine, bromine, cyano, carboxyl, phenyl, phenoxy (where phenyl and phenoxy are optionally substituted by fluorine, chlorine, bromine, cyano, methyl, ethyl, n- or i-propyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl;

and represents phenyl, naphthyl, furyl, thienyl, oxazolyl, isoxazolyl, thiazolyl, isthiazolyl, oxadiazolyl, thiadiazolyl, pyridinyl, pyrimidinyl, pyridazinyl, pyrazinyl, 1,2,3-triazinyl, 1,2,4-triazinyl, 1,3,5-triazinyl, oxiranyl, tetrahydrofuryl, perhydropyranyl, pyrrolidinyl, piperidinyl or morpholinyl, which is in each case mono- to trisubstituted, identically or differently, where the substituents are chosen from the following list:

oxygen (as replacement for two geminal hydrogen atoms), fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl; trimethylene (propane-1,3-diyl), methylenedioxy or ethylenedioxy, which is in each case optionally mono- or polysubstituted, identically or differently, by fluorine, chlorine, methyl, ethyl, n- or i-propyl, or cyclopropyl, cyclobutyl, cyclopentyl or cyclohexyl, and phenyl, phenoxy, benzyl or benzyloxy, which is in each case optionally mono- or polysubstituted, identically or differently, in the phenyl moiety by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy.

3. Compounds according to claim 1 of the general formulae (IA)

(IA)

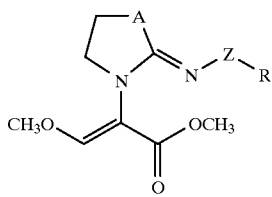

in which A, R and Z have the meanings in claim 1.

4. Compounds of claim 1 of the general formula (IB)

(IB)

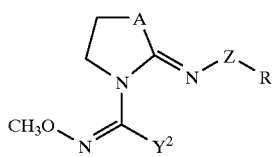

in which

A, R and Z have the meanings mentioned in claim 1 and $Y^2$ represents the groups —CO—OCH$_3$, —CO—NHCH$_3$, —CO—NHOH or

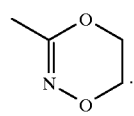

5. Process for the production of pesticides, characterized in that compounds of the formula (I) according to claim 1 are mixed with extenders and/or surface-active agents.

6. Compounds according to claim 1 of the general formulae (IA-1) to (IA-3) and (IB-1) to (IB-3);

(IA-1)

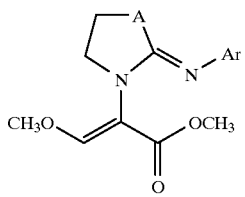

in which

Ar represents in each case optionally mono- to trisubstituted, identically or differently, phenyl or naphthyl, (IA-2)

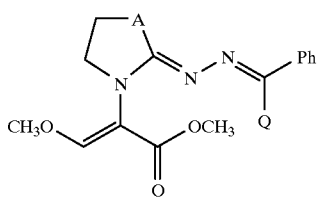

in which

Q represents hydrogen, methyl or cyano, and

Ph represents optionally mono- to trisubstituted, identically or differently, phenyl, (IA-3)

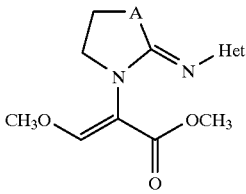

in which

Het represents in each case optionally mono- to trisubstituted, identically or differently, 5- or 6-membered heteroaryl, (IB-1)

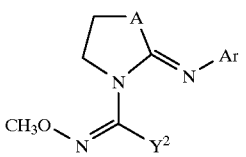

in which $Y^2$ represents the groups —CO—OCH$_3$, —CO—NHCH$_3$, —CO—NHOH or

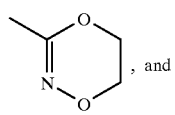, and

Ar represents in each case optionally mono- to trisubstituted, identically or differently, phenyl or naphthyl, (IB-2)

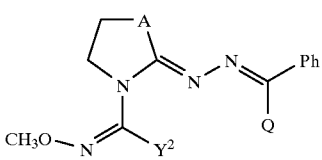

in which

Q represents hydrogen, methyl or cyano, $Y^2$ represents the groups —CO—OCH$_3$, —CO—NHCH$_3$, —CO—NHOH or

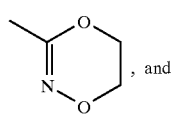, and

Ph represents optionally mono- to trisubstituted, identically or differently, phenyl,

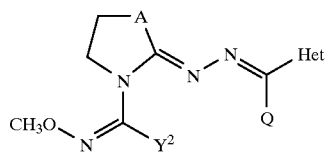

(IB-3)

in which

A has the meaning stated in claim 1, and $Y^2$ represents the groups —CO—OCH$_3$, —CO—NHCH$_3$, —CO—NHOH or

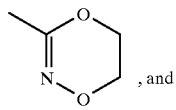, and

Het represents in each case optionally mono- to trisubstituted, identically or differently, 5- or 6-membered heteroaryl.

7. A pesticidal composition comprising a pesticidally effective amount of a compound of the formula (I) according to claim 1 and an extender.

8. A method for controlling pests comprising contacting the pests or their habitat with a pesticidally effective amount of a compound of the formula (I) according to claim 1.

9. A process for preparing a compound of the formula (I) according to claim 1 comprising reacting imino derivatives of the formula (VII)

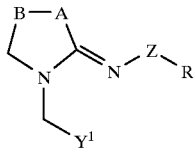

(VII)

in which

A, B, R and Z have the meanings given in claim 1; and $Y^1$ represents the groups —CO-alkyl or —COO-alkyl; initially with methyl formate and subsequently with an alkylating agent in the presence of a diluent and optionally in the presence of a reaction aid.

10. The pesticidal composition according to claim 7, wherein said compound is present in said pesticidal composition in an antifungal effective amount.

11. The method according to claim 8, wherein said method provides a process for controlling fungal infestations.

* * * * *